US012145972B2

(12) United States Patent
Day et al.

(10) Patent No.: US 12,145,972 B2
(45) Date of Patent: *Nov. 19, 2024

(54) NEUREGULIN-4 COMPOUNDS AND METHODS OF USE

(71) Applicant: Eli Lilly and Company, Indianapolis, IN (US)

(72) Inventors: Jonathan Wesley Day, Carmel, IN (US); Josef George Heuer, Carmel, IN (US); Avinash Muppidi, Carmel, IN (US); Wei Ni, Indianapolis, IN (US); James David Pancook, San Diego, CA (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/559,430

(22) Filed: Dec. 22, 2021

(65) Prior Publication Data

US 2022/0112255 A1    Apr. 14, 2022

Related U.S. Application Data

(63) Continuation of application No. 16/835,787, filed on Mar. 31, 2020, now Pat. No. 11,242,370.

(60) Provisional application No. 62/827,386, filed on Apr. 1, 2019.

(51) Int. Cl.
| | | |
|---|---|---|
| A61P 9/04 | (2006.01) | |
| C07K 14/475 | (2006.01) | |
| A61K 38/00 | (2006.01) | |
| A61M 5/142 | (2006.01) | |

(52) U.S. Cl.
CPC .......... *C07K 14/4756* (2013.01); *A61P 9/04* (2018.01); *A61K 38/00* (2013.01); *A61M 5/14248* (2013.01); *C07K 2319/30* (2013.01)

(58) Field of Classification Search
CPC .... A61K 38/1883; A61K 38/00; A61K 45/06; A61K 9/0019; A61P 9/04; A61P 9/00; C07K 14/4756
See application file for complete search history.

(56) References Cited

U.S. PATENT DOCUMENTS

| | | | |
|---|---|---|---|
| 5,530,109 A | 6/1996 | Goodearl et al. | |
| 6,444,642 B1 | 9/2002 | Sklar et al. | |
| 6,635,249 B1 | 10/2003 | Marchionni et al. | |
| 7,037,888 B1 | 5/2006 | Sklar et al. | |
| 7,094,882 B2 | 8/2006 | Harari et al. | |
| 7,115,554 B1 | 10/2006 | Sklar et al. | |
| 7,226,907 B1 | 6/2007 | Zhou | |
| 7,276,587 B2 | 10/2007 | Kavanaugh et al. | |
| 7,384,756 B1 | 6/2008 | Sklar et al. | |
| 7,612,164 B2 | 11/2009 | Zhou | |
| 7,662,772 B2 | 2/2010 | Marchionni et al. | |
| 7,795,212 B2 | 9/2010 | Zhou | |
| 7,964,555 B2 | 6/2011 | Zhou | |
| 7,981,997 B2 | 7/2011 | Harari et al. | |
| 8,026,213 B2 | 9/2011 | Sklar et al. | |
| 8,076,283 B2 | 12/2011 | Marchionni et al. | |
| 8,114,838 B2 | 2/2012 | Marchionni | |
| 8,394,761 B2 | 3/2013 | Marchionni et al. | |
| 8,476,405 B2 | 7/2013 | Zhou | |
| 8,609,620 B2 | 12/2013 | Zhou | |
| 8,785,387 B2 | 7/2014 | Zhou | |
| 8,889,625 B2 | 11/2014 | Liu | |
| 8,933,034 B2 | 1/2015 | Ford | |
| 9,012,400 B2 | 4/2015 | Zhou | |
| 9,029,328 B2 | 5/2015 | Jay et al. | |
| 9,089,524 B2 | 7/2015 | Zhou | |
| 9,198,951 B2 | 12/2015 | Caggiano et al. | |
| 9,340,597 B2 | 5/2016 | Zhou | |
| 9,352,923 B2 | 5/2016 | Cornell et al. | |
| 9,434,777 B2 | 9/2016 | Zhou | |
| 9,555,076 B2 | 1/2017 | Zhou | |
| 9,655,949 B2 | 5/2017 | Zhou | |
| 9,833,497 B2 | 12/2017 | Song et al. | |
| 9,878,010 B2 | 1/2018 | Lin et al. | |
| 10,017,574 B2 | 7/2018 | Tzahor et al. | |
| 10,098,834 B2 * | 10/2018 | Zhou | A61K 38/1883 |
| 11,242,370 B2 * | 2/2022 | Day | A61P 9/04 |
| 2008/0025983 A1 | 1/2008 | Adams et al. | |
| 2009/0156488 A1 | 6/2009 | Zhou | |
| 2010/0048863 A1 | 2/2010 | Harari et al. | |
| 2010/0055093 A1 | 3/2010 | Shepard et al. | |
| 2012/0121557 A1 | 5/2012 | Kuhn | |
| 2013/0078235 A1 | 3/2013 | Zhou | |
| 2014/0364366 A1 | 12/2014 | Zhou | |

(Continued)

FOREIGN PATENT DOCUMENTS

| | | |
|---|---|---|
| EP | 2319529 A1 | 4/2000 |
| EP | 3087997 A1 | 4/2000 |

(Continued)

OTHER PUBLICATIONS

Harari et al. Neuregulin-4: a novel growth factor that acts through the ErbB-4 receptor tyrosine kinase. Oncogene (1999) 18, 2681-2689. (Year: 1999).*

Diaz-Herráez, P., et al. (2017). Transplantation of adipose-derived stem cell combined with neuregulin-microparticles promotes efficient cardiac repair in a rat myocardial infarction model. *Journal of Controlled Release*, 249, 23-31.

Pascual-Gil, S., et al. (2017). Cytokine-loaded PLGA and PEG-PLGA microparticles showed similar heart regeneration in a rat myocardial infarction model. *International journal of pharmaceutics*, 523(2), 531-533.

Formiga, F. R., et al. (2014). Controlled delivery of fibroblast growth factor-1 and neuregulin-1 from biodegradable microparticles promotes cardiac repair in a rat myocardial infarction model through activation of endogenous regeneration. *Journal of Controlled Release*, 173, 132-139.

(Continued)

*Primary Examiner* — Aradhana Sasan
*Assistant Examiner* — Jia-Hai Lee
(74) *Attorney, Agent, or Firm* — Matthew T. Lord

(57) ABSTRACT

The present invention relates to neuregulin (NRG) 4 compounds and methods of treatment with NRG4 compounds.

29 Claims, No Drawings

Specification includes a Sequence Listing.

(56) References Cited

U.S. PATENT DOCUMENTS

| | | |
|---|---|---|
| 2015/0183844 A1 | 7/2015 | Ford |
| 2015/0284440 A1 | 10/2015 | Zhou |
| 2015/0343023 A1 | 12/2015 | Jay et al. |
| 2016/0095903 A1 | 4/2016 | Zhou |
| 2017/0007671 A1 | 1/2017 | Zhou |
| 2017/0232068 A1 | 8/2017 | Zhou |
| 2017/0333529 A1 | 11/2017 | Vermeulen et al. |
| 2017/0368140 A1 | 12/2017 | Zhou |
| 2018/0104311 A1 | 4/2018 | Zhou |
| 2018/0318391 A1 | 11/2018 | Frey |

FOREIGN PATENT DOCUMENTS

| | | | |
|---|---|---|---|
| EP | 2918283 | A1 | 12/2006 |
| ES | 2315110 | A1 | 3/2009 |
| JP | 5809789 | B2 | 11/2015 |
| WO | 199918976 | A1 | 4/1999 |
| WO | 200064400 | A2 | 11/2000 |
| WO | 200114415 | A2 | 3/2001 |
| WO | 200189568 | A1 | 11/2001 |
| WO | 2001081540 | A2 | 11/2001 |
| WO | 2003014159 | A2 | 2/2003 |
| WO | 2003025142 | A2 | 3/2003 |
| WO | 2003099300 | A1 | 12/2003 |
| WO | 2005017096 | A2 | 2/2005 |
| WO | 2007076701 | A1 | 7/2007 |
| WO | 2008006922 | A1 | 1/2008 |
| WO | 2009033373 | A1 | 3/2009 |
| WO | 2010019275 | A2 | 2/2010 |
| WO | 2010030317 | A2 | 3/2010 |
| WO | 2010060266 | A1 | 6/2010 |
| WO | 2010142141 | A1 | 12/2010 |
| WO | 2011011388 | A2 | 1/2011 |
| WO | 2011119836 | A1 | 9/2011 |
| WO | 2013053076 | A1 | 4/2013 |
| WO | 2013053158 | A1 | 4/2013 |
| WO | 2014051567 | A1 | 4/2014 |
| WO | 2014138502 | A1 | 9/2014 |
| WO | 2014153385 | A1 | 9/2014 |
| WO | 2014153385 | A2 | 9/2014 |
| WO | 2015158743 | A1 | 10/2015 |
| WO | 2016058493 | A1 | 4/2016 |
| WO | 2017058828 | A1 | 4/2017 |
| WO | 2019200033 | A1 | 10/2019 |

OTHER PUBLICATIONS

Vullhorst, D., et al. (2017). Structural similarities between neuregulin 1-3 isoforms determine their subcellular distribution and signaling mode in central neurons. *Journal of Neuroscience*, 37(21), 5232-5249.

Harari, D., et al. (1999). Neuregulin-4: a novel growth factor that acts through the ErbB-4 receptor tyrosine kinase. *Oncogne*, 18(17), 2681-2689.

Hayes, N. V., et al. (2008). Characterization of the cell membrane-association products of the Neuregulin 4 Gene. *Oncogene*, 27(5), 715-720.

Hayes, N. V., et al. (2011). Expression of neuregulin 4 splice variants in normal human tissues and prostate cancer and their effect on cell motility. *Endcorine-related cancer*, 18(1), 39.

Hayes, N. V., et al. (2007). Identification and characterization fo novel spliced variants of neuregulin 4 in prostate cancer. *Clinical cancer research*, 13(11), 3147-3155.

ClinicalTrials.Gov, Study of JK07 in Subjects With Heart Failure with Reduced Ejection Fraction, Dec. 24, 2019.

Gemberling, M., et al. (2015). Nrg1 is an injury-induced cardiomyocyte mitogen for the endogenous heart regeneration program in zebrafish. *Elife*, 4.

Patent Cooperation Treaty Written Opinion of the International Searching Authority pretaining to International Application No. PCT/US2020/025921; International Filing Date: Mar. 31, 2020; Date of Mailing: Aug. 17, 2020.

Diaz-Herráez, P., et al. (2017). Transplantation of adipose-derived stem cells combined with neuregulin-microparticles promotes efficient cardiac repair in a rat myocardial infarction model. *Journal of Controlled Release*, 249, 23-31.

Pascual-Gil, S., et al. (2017). Cytokine-loaded PLGA and PEG-PLGA micropanicles showed similar heart regeneration in a rat myocardial infarction model. *International journal of pharmaceutics*, 523(2), 531-533.

Ganapathy, B., et al. (2016). Neuregulin-1 administration protocols sufficient for stimulating cardiac regeneration in young mice do not induce somatic, organ, or neoplastic growth. *PLoS one*, 11(5).

Cai MX, et al. Exercise training activates neuregulin 1/ErbB signaling and promotes cardiac repair in a rat myocardial infarction model. Life Sci 2016; 15(149): 1-9.

Polizzotti, B. D., et al. (2015). Neuregulin stimulation of cardiomyocyte regeneration in mice and human myocardium reveals a therapeutic window. *Science translational medicine*, 7(281), 281ra45-281ra45.

D'Uva, G., et al. (2015). ERBB2 triggers mammalian heart regeneration by promoting cardiomyocyte dedifferentiation and proliferation. *Nature cell biology*, 17(5), 627-638.

Formiga, F. R., et al. (2014). Controlled delivery of fibroblast growth factor-1 and neuregulin-1 from biodegradable microparticies promotes cardiac repair in a rat myocardiai infarction model through activation of endogenous regeneration. *Journal of Controlled Release*, 173, 132-139.

Lenihan, D. J., et al. (2016). A phase I, single ascending dose study of cimaglermin alfa (neuregulin 1β3) in patients with systolic dysfunction and heart failure. *JACC: Basic to Translational Science*, 1(7), 576-586.

Vullhorst, D., et al. (2017). Structural simiiarities between neuregulin 1-3 isoforms determine their subcellular distribution and signaling mode in central neurons. *Journal of Neuroscience*, 37(21), 5232-5249.

Yutzey, K. E. (2015). Regenerative biology: Neuregulin 1 makes heart muscle. *Nature*, 520(7548), 445-446.

Bersell, K., et al. (2009). Neuregulin1/ErbB4 signaling induces cardiomyocyte proliferation and repair of heart injury. *Cell*, 138(2), 257-270.

Harvey, R. P., et al. (2016). Cardiac Regeneration Therapies—Targeting Neuregulin 1 Signalling *Heart, Lung and Circulation*, 25(1), 4-7.

Tzahor, E., & Poss, K. D. (2017). Cardiac regeneration strategies: staying young at heart, *Science*, 356(6342), 1035-1039.

Bergmann, O., et al. (2009). Evidence for cardiomyocyte renewal in humans. *Science*, 324(5923), 98-102.

Hashimoto, H., et al. (2018). Therapeutic approaches for cardiac regeneration and repair. *Nature Reviews Cardiology*, 15(10), 585-600.

Hariri, D., et al. (1999). Neuregulin-r: a novel growth factor that acts through the ErbB-4 receptor tyrosine kinase. *Oncogene*, 18(17), 2681-2689.

Hayes, N. V., et al. (2008). Characterization of the cell membrane-associated products of the Neuregulin 4 gene. *Oncogene*, 27(5), 715-720.

Hayes, N. V., et al. (2011) Expression of neureguiin 4 splice variants in normal human tissues and prostate cancer and their effects on cell motility. *Endocrine-related cancer*, 18(1), 39.

Hayes, N. V., et al. (2007). Identification and characterization of novel spliced variants of neuregulin 4 in prostate cancer. *Clinical cancer research*, 13(11), 3147-3155.

Ginsberg, B. H. (2019). Patch pumps for insulin. *Journal of diabetes science and technology*, 13(1), 27-33.

ClinicalTrials.Gov, Study of JK07 in Subjects With Heart Failure With Reduced Ejection Fraction (HFrEF), Dec. 24, 2019.

Gemberling, M., et al. (2015). Nrg1 is an injury-induced cardiomyocyte mitogen for the endogenous heart regeneration program in zebrafish. *Elife*, 4, e05871.

Patent Cooperation Treaty International Search Report pertaining to International Application No. PCT/US2020/025921; International Filing Date: Mar. 31, 2020; Date of Mailing: Aug. 17, 2020.

(56) References Cited

OTHER PUBLICATIONS

Patent Cooperation Treaty Written Opinion of the International Searching Authority pertaining to International Application No. PCT/US2020/025921; International Filing Date: Mar. 31, 2020; Date of Mailing: Aug. 17, 2020.

* cited by examiner

SEQUENCE LISTING

<160> NUMBER OF SEQ ID NOS: 20

<210> SEQ ID NO 1
<211> LENGTH: 47
<212> TYPE: PRT
<213> ORGANISM: Homo sapiens

<400> SEQUENCE: 1

Asp His Glu Glu Pro Cys Gly Pro Ser His Lys Ser Phe Cys Leu Asn
1               5                   10                  15

Gly Gly Leu Cys Tyr Val Ile Pro Thr Ile Pro Ser Pro Phe Cys Arg
            20                  25                  30

Cys Val Glu Asn Tyr Thr Gly Ala Arg Cys Glu Glu Val Phe Leu
        35                  40                  45

<210> SEQ ID NO 2
<211> LENGTH: 47
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa at position 8 is E or P
<220> FEATURE:
<221> NAME/KEY: MISC_FEATURE
<222> LOCATION: (22)..(22)
<223> OTHER INFORMATION: Xaa at position 22 is Q or V
<220> FEATURE:
<221> NAME/KEY: MISC_FEATURE
<222> LOCATION: (26)..(26)
<223> OTHER INFORMATION: Xaa at position 26 is F or I

```
<220> FEATURE:
<221> NAME/KEY: MISC_FEATURE
<222> LOCATION: (35)..(35)
<223> OTHER INFORMATION: Xaa at position 35 is E or A
<220> FEATURE:
<221> NAME/KEY: MISC_FEATURE
<222> LOCATION: (44)..(44)
<223> OTHER INFORMATION: Xaa at position 44 is H, K or E

<400> SEQUENCE: 2

Gly His Glu Glu Pro Cys Gly Xaa Ser His Lys Ser Phe Cys Leu Asn
1               5                   10                  15

Gly Gly Leu Cys Tyr Xaa Ile Pro Thr Xaa Pro Ser Pro Phe Cys Arg
            20                  25                  30

Cys Val Xaa Asn Tyr Thr Gly Ala Arg Cys Glu Xaa Val Phe Leu
        35                  40                  45

<210> SEQ ID NO 3
<211> LENGTH: 115
<212> TYPE: PRT
<213> ORGANISM: Artificial Sequence
<220> FEATURE:
<223> OTHER INFORMATION: Synthetic Construct

<400> SEQUENCE: 3

Met Pro Thr Asp His Glu Glu Pro Cys Gly Pro Ser His Lys Ser Phe
1               5                   10                  15

Cys Leu Asn Gly Gly Leu Cys Tyr Val Ile Pro Thr Ile Pro Ser Pro
            20                  25                  30

Phe Cys Arg Cys Val Glu Asn Tyr Thr Gly Ala Arg Cys Glu Glu Val
        35                  40                  45

Phe Leu Pro Gly Ser Ser Ile Gln Thr Lys Ser Asn Leu Phe Glu Ala
    50                  55                  60

Phe Val Ala Leu Ala Val Leu Val Thr Leu Ile Ile Gly Ala Phe Tyr
65                  70                  75                  80

Phe Leu Cys Arg Lys Gly His Phe Gln Arg Ala Ser Ser Val Gln Tyr
                85                  90                  95

Asp Ile Asn Leu Val Glu Thr Ser Ser Thr Ser Ala His His Ser His
            100                 105                 110

Glu Gln His
        115

<210> SEQ ID NO 4
<211> LENGTH: 47
<212> TYPE: PRT
<213> ORGANISM: Artificial Sequence
<220> FEATURE:
<223> OTHER INFORMATION: Synthetic Construct

<400> SEQUENCE: 4

Gly His Glu Glu Pro Cys Gly Pro Ser His Lys Ser Phe Cys Leu Asn
1               5                   10                  15

Gly Gly Leu Cys Tyr Gln Ile Pro Thr Ile Pro Ser Pro Phe Cys Arg
            20                  25                  30

Cys Val Glu Asn Tyr Thr Gly Ala Arg Cys Glu Lys Val Phe Leu
        35                  40                  45

<210> SEQ ID NO 5
<211> LENGTH: 5
<212> TYPE: PRT
<213> ORGANISM: Artificial Sequence
<220> FEATURE:
```

```
<223> OTHER INFORMATION: Synthetic Construct
<220> FEATURE:
<221> NAME/KEY: VARIANT
<222> LOCATION: (1)..(5)
<223> OTHER INFORMATION: SEQ ID NO:5 is further represented as
      (GGGGXlambda)n, wherein: Xlambda is Q, A, E or S; and n is 1-5.
<220> FEATURE:
<221> NAME/KEY: VARIANT
<222> LOCATION: (5)..(5)
<223> OTHER INFORMATION: Xaa at position 5 is Xlambda wherein Xlambda is
      Q, A, E or S

<400> SEQUENCE: 5

Gly Gly Gly Gly Xaa
1               5

<210> SEQ ID NO 6
<211> LENGTH: 221
<212> TYPE: PRT
<213> ORGANISM: Artificial Sequence
<220> FEATURE:
<223> OTHER INFORMATION: Synthetic Construct

<400> SEQUENCE: 6

Glu Cys Pro Pro Cys Pro Ala Pro Pro Val Ala Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Gln Phe Asn Trp Tyr Val Asp Gly Val Glu Val His Asn Ala Lys Thr
    50                  55                  60

Lys Pro Arg Glu Glu Gln Phe Asn Ser Thr Phe Arg Val Val Ser Val
65                  70                  75                  80

Leu Thr Val Val His Gln Asp Trp Leu Asn Gly Lys Glu Tyr Lys Cys
                85                  90                  95

Lys Val Ser Asn Lys Gly Leu Pro Ala Pro Ile Glu Lys Thr Ile Ser
            100                 105                 110

Lys Thr Lys Gly Gln Pro Arg Glu Pro Gln Val Tyr Thr Leu Pro Pro
        115                 120                 125

Ser Arg Glu Glu Met Thr Lys Asn Gln Val Ser Leu Trp Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly
    210                 215                 220

<210> SEQ ID NO 7
<211> LENGTH: 221
<212> TYPE: PRT
<213> ORGANISM: Artificial Sequence
<220> FEATURE:
<223> OTHER INFORMATION: Synthetic Construct

<400> SEQUENCE: 7
```

```
Glu Cys Pro Pro Cys Pro Ala Pro Pro Val Ala Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
            35                  40                  45

Gln Phe Asn Trp Tyr Val Asp Gly Val Glu Val His Asn Ala Lys Thr
        50                  55                  60

Lys Pro Arg Glu Glu Gln Phe Asn Ser Thr Phe Arg Val Val Ser Val
65                  70                  75                  80

Leu Thr Val Val His Gln Asp Trp Leu Asn Gly Lys Glu Tyr Lys Cys
                85                  90                  95

Lys Val Ser Asn Lys Gly Leu Pro Ala Pro Ile Glu Lys Thr Ile Ser
                100                 105                 110

Lys Thr Lys Gly Gln Pro Arg Glu Pro Gln Val Tyr Thr Leu Pro Pro
            115                 120                 125

Ser Arg Glu Glu Met Thr Lys Asn Gln Val Ser Leu Ser Cys Ala Val
        130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Val Ser Lys Leu Thr Val Asp Lys Ser Arg Trp
                180                 185                 190

Gln Gln Gly Asn Val Phe Ser Cys Ser Val Met His Glu Ala Leu His
            195                 200                 205

Asn His Tyr Thr Gln Lys Ser Leu Ser Leu Ser Pro Gly
        210                 215                 220

<210> SEQ ID NO 8
<211> LENGTH: 221
<212> TYPE: PRT
<213> ORGANISM: Artificial Sequence
<220> FEATURE:
<223> OTHER INFORMATION: Synthetic Construct

<400> SEQUENCE: 8

Glu Cys Pro Pro Cys Pro Ala Pro Pro Val Ala Gly Pro Ser Val Phe
1               5                   10                  15

Leu Phe Pro Pro Lys Pro Lys Asp Thr Leu Met Ala Ser Arg Thr Pro
            20                  25                  30

Glu Val Thr Cys Val Val Val Asp Val Ser His Glu Asp Pro Glu Val
            35                  40                  45

Gln Phe Asn Trp Tyr Val Asp Gly Val Glu Val His Asn Ala Lys Thr
        50                  55                  60

Lys Pro Arg Glu Glu Gln Phe Asn Ser Thr Phe Arg Val Val Ser Val
65                  70                  75                  80

Leu Thr Val Val His Gln Asp Trp Leu Asn Gly Lys Glu Tyr Lys Cys
                85                  90                  95

Lys Val Ser Asn Lys Gly Leu Pro Ala Pro Ile Glu Lys Thr Ile Ser
                100                 105                 110

Lys Thr Lys Gly Gln Pro Arg Glu Pro Gln Val Tyr Thr Leu Pro Pro
            115                 120                 125

Ser Arg Glu Glu Met Thr Lys Asn Gln Val Ser Leu Trp Cys Leu Val
        130                 135                 140
```

```
Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn Ala Tyr Thr Gln Lys Ser Leu Ser Leu Ser Pro Gly
    210                 215                 220
```

<210> SEQ ID NO 9
<211> LENGTH: 221
<212> TYPE: PRT
<213> ORGANISM: Artificial Sequence
<220> FEATURE:
<223> OTHER INFORMATION: Synthetic Construct

<400> SEQUENCE: 9

```
Glu Cys Pro Pro Cys Pro Ala Pro Pro Val Ala Gly Pro Ser Val Phe
1               5                   10                  15

Leu Phe Pro Pro Lys Pro Lys Asp Thr Leu Met Ala Ser Arg Thr Pro
                20                  25                  30

Glu Val Thr Cys Val Val Val Asp Val Ser His Glu Asp Pro Glu Val
            35                  40                  45

Gln Phe Asn Trp Tyr Val Asp Gly Val Glu Val His Asn Ala Lys Thr
    50                  55                  60

Lys Pro Arg Glu Glu Gln Phe Asn Ser Thr Phe Arg Val Val Ser Val
65                  70                  75                  80

Leu Thr Val Val His Gln Asp Trp Leu Asn Gly Lys Glu Tyr Lys Cys
                85                  90                  95

Lys Val Ser Asn Lys Gly Leu Pro Ala Pro Ile Glu Lys Thr Ile Ser
            100                 105                 110

Lys Thr Lys Gly Gln Pro Arg Glu Pro Gln Val Tyr Thr Leu Pro Pro
        115                 120                 125

Ser Arg Glu Glu Met Thr Lys Asn Gln Val Ser Leu Ser Cys Ala Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Val Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn Ala Tyr Thr Gln Lys Ser Leu Ser Leu Ser Pro Gly
    210                 215                 220
```

<210> SEQ ID NO 10
<211> LENGTH: 62
<212> TYPE: PRT
<213> ORGANISM: Artificial Sequence
<220> FEATURE:
<223> OTHER INFORMATION: Synthetic Construct

<400> SEQUENCE: 10

```
Gly Gly Gly Gly Ser Gly Gly Gly Ser Gly Gly Gly Gly Ser Gly
1               5                   10                  15
```

His Glu Glu Pro Cys Gly Pro Ser His Lys Ser Phe Cys Leu Asn Gly
                20                  25                  30

Gly Leu Cys Tyr Val Ile Pro Thr Ile Pro Ser Pro Phe Cys Arg Cys
            35                  40                  45

Val Glu Asn Tyr Thr Gly Ala Arg Cys Glu Glu Val Phe Leu
    50                  55                  60

<210> SEQ ID NO 11
<211> LENGTH: 62
<212> TYPE: PRT
<213> ORGANISM: Artificial Sequence
<220> FEATURE:
<223> OTHER INFORMATION: Synthetic Construct

<400> SEQUENCE: 11

Gly Gly Gly Gly Ser Gly Gly Gly Ser Gly Gly Gly Gly Ser Gly
1               5                   10                  15

His Glu Glu Pro Cys Gly Glu Ser His Lys Ser Phe Cys Leu Asn Gly
                20                  25                  30

Gly Leu Cys Tyr Val Ile Pro Thr Ile Pro Ser Pro Phe Cys Arg Cys
            35                  40                  45

Val Glu Asn Tyr Thr Gly Ala Arg Cys Glu Glu Val Phe Leu
    50                  55                  60

<210> SEQ ID NO 12
<211> LENGTH: 62
<212> TYPE: PRT
<213> ORGANISM: Artificial Sequence
<220> FEATURE:
<223> OTHER INFORMATION: Synthetic Construct

<400> SEQUENCE: 12

Gly Gly Gly Gly Ser Gly Gly Gly Ser Gly Gly Gly Gly Ser Gly
1               5                   10                  15

His Glu Glu Pro Cys Gly Pro Ser His Lys Ser Phe Cys Leu Asn Gly
                20                  25                  30

Gly Leu Cys Tyr Gln Ile Pro Thr Ile Pro Ser Pro Phe Cys Arg Cys
            35                  40                  45

Val Glu Asn Tyr Thr Gly Ala Arg Cys Glu Glu Val Phe Leu
    50                  55                  60

<210> SEQ ID NO 13
<211> LENGTH: 62
<212> TYPE: PRT
<213> ORGANISM: Artificial Sequence
<220> FEATURE:
<223> OTHER INFORMATION: Synthetic Construct

<400> SEQUENCE: 13

Gly Gly Gly Gly Ser Gly Gly Gly Ser Gly Gly Gly Gly Ser Gly
1               5                   10                  15

His Glu Glu Pro Cys Gly Pro Ser His Lys Ser Phe Cys Leu Asn Gly
                20                  25                  30

Gly Leu Cys Tyr Val Ile Pro Thr Phe Pro Ser Pro Phe Cys Arg Cys
            35                  40                  45

Val Glu Asn Tyr Thr Gly Ala Arg Cys Glu Glu Val Phe Leu
    50                  55                  60

<210> SEQ ID NO 14
<211> LENGTH: 62

<212> TYPE: PRT
<213> ORGANISM: Artificial Sequence
<220> FEATURE:
<223> OTHER INFORMATION: Synthetic Construct

<400> SEQUENCE: 14

Gly Gly Gly Gly Ser Gly Gly Gly Ser Gly Gly Gly Ser Gly
1               5                   10                  15

His Glu Glu Pro Cys Gly Pro Ser His Lys Ser Phe Cys Leu Asn Gly
            20                  25                  30

Gly Leu Cys Tyr Val Ile Pro Thr Ile Pro Ser Pro Phe Cys Arg Cys
        35                  40                  45

Val Ala Asn Tyr Thr Gly Ala Arg Cys Glu Glu Val Phe Leu
    50                  55                  60

<210> SEQ ID NO 15
<211> LENGTH: 62
<212> TYPE: PRT
<213> ORGANISM: Artificial Sequence
<220> FEATURE:
<223> OTHER INFORMATION: Synthetic Construct

<400> SEQUENCE: 15

Gly Gly Gly Gly Ser Gly Gly Gly Ser Gly Gly Gly Ser Gly
1               5                   10                  15

His Glu Glu Pro Cys Gly Pro Ser His Lys Ser Phe Cys Leu Asn Gly
            20                  25                  30

Gly Leu Cys Tyr Val Ile Pro Thr Phe Pro Ser Pro Phe Cys Arg Cys
        35                  40                  45

Val Glu Asn Tyr Thr Gly Ala Arg Cys Glu Lys Val Phe Leu
    50                  55                  60

<210> SEQ ID NO 16
<211> LENGTH: 62
<212> TYPE: PRT
<213> ORGANISM: Artificial Sequence
<220> FEATURE:
<223> OTHER INFORMATION: Synthetic Construct

<400> SEQUENCE: 16

Gly Gly Gly Gly Ser Gly Gly Gly Ser Gly Gly Gly Ser Gly
1               5                   10                  15

His Glu Glu Pro Cys Gly Pro Ser His Lys Ser Phe Cys Leu Asn Gly
            20                  25                  30

Gly Leu Cys Tyr Val Ile Pro Thr Phe Pro Ser Pro Phe Cys Arg Cys
        35                  40                  45

Val Glu Asn Tyr Thr Gly Ala Arg Cys Glu His Val Phe Leu
    50                  55                  60

<210> SEQ ID NO 17
<211> LENGTH: 62
<212> TYPE: PRT
<213> ORGANISM: Artificial Sequence
<220> FEATURE:
<223> OTHER INFORMATION: Synthetic Construct

<400> SEQUENCE: 17

Gly Gly Gly Gly Ser Gly Gly Gly Ser Gly Gly Gly Ser Gly
1               5                   10                  15

His Glu Glu Pro Cys Gly Glu Ser His Lys Ser Phe Cys Leu Asn Gly
            20                  25                  30

```
Gly Leu Cys Tyr Val Ile Pro Thr Phe Pro Ser Pro Phe Cys Arg Cys
             35                  40                  45

Val Glu Asn Tyr Thr Gly Ala Arg Cys Glu Glu Val Phe Leu
 50                  55                  60
```

<210> SEQ ID NO 18
<211> LENGTH: 52
<212> TYPE: PRT
<213> ORGANISM: Artificial Sequence
<220> FEATURE:
<223> OTHER INFORMATION: Synthetic Construct

<400> SEQUENCE: 18

```
Gly Gly Gly Gly Ser Gly His Glu Glu Pro Cys Gly Pro Ser His Lys
 1               5                  10                  15

Ser Phe Cys Leu Asn Gly Gly Leu Cys Tyr Gln Ile Pro Thr Ile Pro
             20                  25                  30

Ser Pro Phe Cys Arg Cys Val Glu Asn Tyr Thr Gly Ala Arg Cys Glu
             35                  40                  45

Lys Val Phe Leu
 50
```

<210> SEQ ID NO 19
<211> LENGTH: 62
<212> TYPE: PRT
<213> ORGANISM: Artificial Sequence
<220> FEATURE:
<223> OTHER INFORMATION: Synthetic Construct

<400> SEQUENCE: 19

```
Gly Gly Gly Gly Ser Gly Gly Gly Ser Gly Gly Gly Ser Gly
 1               5                  10                  15

His Glu Glu Pro Cys Gly Pro Ser His Lys Ser Phe Cys Leu Asn Gly
             20                  25                  30

Gly Leu Cys Tyr Gln Ile Pro Thr Ile Pro Ser Pro Phe Cys Arg Cys
             35                  40                  45

Val Glu Asn Tyr Thr Gly Ala Arg Cys Glu Lys Val Phe Leu
 50                  55                  60
```

<210> SEQ ID NO 20
<211> LENGTH: 4
<212> TYPE: PRT
<213> ORGANISM: Artificial Sequence
<220> FEATURE:
<223> OTHER INFORMATION: Synthetic Construct

<400> SEQUENCE: 20

```
Gly Gly Gly Ser
 1
```

NEUREGULIN-4 COMPOUNDS AND METHODS OF USE

The specification incorporates by reference the Sequence Listing submitted Aug. 4, 2020. Pursuant to 37 C.F.R. § 1.52(e) (5), the Sequence Listing text file, identified as X2215321Jul2020v2.txt, is 6 KB and was created on Jul. 23, 2020. The Sequence Listing, electronically filed herewith, does not extend beyond the scope of the specification and thus does not contain new matter.

The present invention relates to neuregulin (NRG) 4 compounds and methods of treatment with NRG4 compounds. The NRG4 compounds of the present invention preferably have potent binding to the human epidermal grown factor receptor (HER) 4, and potent activity associated with that binding. The preferred NRG4 compounds may be useful for improving cardiac function and/or treating diseases in which HER4 binding and resulting activity play a prominent role, such as heart failure (HF), including HF with reduced ejection fraction (HFrEF).

There is an unmet medical need for new and improved treatments for HF. Currently available therapies are intended to slow down disease progression and improve symptoms, and rely on hemodynamic changes to reduce the workload of the failing heart. These therapies include agents intended to: (a) reduce heart rate, such as beta blockers and ivabradine; (b) reduce blood pressure, such as angiotensin-converting enzyme (ACE) inhibitors, angiotensin II receptor blockers (ARB), mineralocorticoid receptor antagonists (MRA), and sacubitril/valsartan (ENTRESTO®); and/or (c) treat or prevent volume overload, such as diuretics and MRA. These treatments, however, do not directly treat the heart, and have practical limitations, such as requiring dose titration and monitoring for hypotension. In addition, even with these existing treatment options available, all HF patients, even those who are mildly symptomatic are at high risk of dying. See, e.g., Ahmed A, *A propensity matched study of New York Heart Association class and natural history end points in heart failure*, AM. J. CARDIOL. 2007; 99(4):549-553. Thus, new and improved HF treatments are needed.

Research and development efforts to identify new treatment options have been undertaken. For example, WO2014/187342 purports to describe preventing, treating, or delaying HF through extended release of NRG, which is stated to include NRG1, NRG2, NRG3 and NRG4. The publication also describes a clinical study which was purportedly conducted on extended administration of NRG-1 in patients with chronic heart failure.

Nevertheless, the need remains for treatment options with improved efficacy and reduced risk for toxicity as compared to existing therapies. There is a need for therapies that improve long-term outcomes, including increased survival and reduced hospitalization rates. There is also a need for therapies that improve cardiac function, with the potential to modify or reverse the disease, through mechanisms other than alteration of hemodynamics. There is also a need for better-tolerated therapies, including in particular with respect to treatment in patients with comorbidities such as hypotension, hypokalemia and renal dysfunction. There is also a need for therapies which improve quality of life (QOL) in patients with advanced disease. The present invention seeks to meet one or more of these critical unmet needs.

Accordingly, the present invention provides NRG4 compounds with activity associated with selective binding to HER4. The NRG4 compounds of the present invention have little to no binding to HER3, resulting in reduced risk of toxicity and/or tolerability issues associated with HER3.

The present invention also provides methods of using NRG4 compounds to treat or prevent CVD and related conditions, including in particular HF. Preferred NRG4 compounds and methods of the present invention reduce the risk of CV-related death or HF-related hospitalization, reduce the risk of myocardial infarction (MI) or stroke, reduce the probability of a need for left ventricular assist device (LVAD) or cardiac transplant, improve cardiac function and structure, and/or improve the symptoms and physical limitations associated with HF, leading to improvements in QoL. Preferred NRG4 compounds and methods can be used in combination with standard of care (SoC) without the need for titration or monitoring, and do not increase hypotension, worsen renal function, result in electrolyte imbalance, contribute to liver dysfunction, increase incidence of tumors, and/or lead to persistent hypospermia.

The present invention also provides NRG4 compounds comprising modification of the D residue at position 1 to a G residue and up to five additional modifications as compared to the amino acid sequence of human NRG4 (SEQ ID NO:1).

The present invention also provides NRG4 compounds comprising the formula: $X_0GHEEPCGX_8SHKSFCL\text{-}NGGLCYX_{22}IPTX_{26}PSPFCRCVX_{35}NYTGARCEX_{44}VFL$, wherein: $X_0$ is selected from the group consisting of T, PT, MPT, S, GS, GGS, GGGS, and $(GGGGX_\lambda)_n$ wherein $X_\lambda$ is Q, A, E or S and n=1-5 (SEQ ID NO:5), or is absent; $X_8$ is E or P; $X_{22}$ is Q or V; $X_{26}$ is F or I; $X_{35}$ is E or A; and $X_{44}$ is H, K or E (SEQ ID NO:2).

In another aspect, the present invention provides a method of treating or preventing HFrEF in a patient in need thereof, comprising administering to the patient a therapeutically effective amount of an NRG4 compound for 24-96 hours.

Another embodiment of the present invention provides an NRG4 compound of the present invention for use in therapy.

Another embodiment of the present invention provides an NRG4 compound for use in treating or preventing HFrEF, wherein the NRG4 compound is administered for 24-96 hours.

Another embodiment of the present invention provides an NRG4 compound for use in the manufacture of a medicament for the treatment or prevention of HFrEF, wherein the NRG4 compound is administered for 24-96 hours.

Another embodiment of the present invention provides a pharmaceutical composition comprising an NRG4 compound of the present invention and a pharmaceutically acceptable carrier, diluent, or excipient.

Another embodiment of the present invention provides a pump device comprising an NRG4 compound of the present invention. In certain embodiments, the pump is a patch pump.

NRG4 is one of four members of the NRG family of proteins, which are themselves part of a larger family of proteins known as epidermal growth factor (EGF) proteins. The EGF family of proteins includes EGF itself, as well as other proteins, known as EGF-like proteins, which share certain structural features similar to EGF. EGF-like proteins include NRG1, NRG2, NRG3 and NRG4, as well as heparin-binding EGF-like growth factor (HB-EGF), transforming growth factor-α, amphiregulin (AR), epiregulin (EPR), epigen, betacellulin (BTC) and various isoforms of these proteins. While these ligands are extracellular membrane proteins, various cellular stimuli result in cellular metalloprotease activation resulting in proteolytic release of the EGF domain of the protein which is then free to bind to receptor and initiate signaling. The various members of the EGF family of proteins have a broad array of diverse development-related effects, including effects relating to both normal development as well as the pathology of many diseases, including cancer. The effects are mediated through interactions with a subfamily of four receptor tyrosine kinases referred to as the ErbB family of receptors: EGFR (ErbB-1), HER2 (ErbB-2), HER3 (ErbB-3), HER4 (ErbB-4), and isoforms of these receptors. The members of the NRG family themselves have different effects mediated through their particular interactions with EGFR, HER3 and HER4. While HER2 does not bind the members of the NRG family, HER2 does facilitate downstream signaling by forming heterodimers with EGFR, HER3 and HER4 once they are liganded. Thus, references made herein to HER3 (or HER3/2 or HER2/3) or HER4 (or HER4/2 or HER2/4) activity should be understood as the activity that results from the of downstream signaling following binding of a ligand, such as a member of the NRG family, to either HER3 or HER4, and the subsequent heterodimerization of that bound receptor with HER2.

As noted above, different members of the NRG family have different effects mediated by different receptor affinity and activity profiles. For example, NRG1 compounds interact with the extracellular domains of HER3 and HER4, and play a role in normal development of multiple organs and in the pathogenesis of cancer. HER4 binding, and the activity resulting therefrom, has been associated with cardiac function and structure improvement, while HER3 binding, and the activity resulting therefrom, has been associated with cancer, nausea, diarrhea and hepatotoxicity. See, e.g., O'Shea S, Johnson K, Clark R, Sliwkowski M X, Erickson S L. *Effects of in vivo heregulin beta1 treatment in wild type and ErbB gene-targeted mice depend on receptor levels and pregnancy*. AM J PATHOL. 2001; 158(5):1871-80; Mendes-Ferreira P, De Keulenaer G W, Leite-Moreira A F, Brás-Silva C. *Therapeutic potential of neuregulin-1 in cardiovascular disease*. DRUG DISCOV TODAY. 2013; 18(17-18):836-42. Review. NRG4 on the other hand binds and activates HER4 but has little to no binding to or activity at HER3.

NRG4 is expressed as a 115 amino acid precursor protein having the sequence set forth in SEQ ID NO:3:
MPTDHEEPCG PSHKSFCLNG GLCYVIPTIP SPFCRCVENY TGARCEEVFL PGSSIQTKSN LFEAFVALAV LVTLIIGAFY FLCRKGHFQR ASSVQYDINL VETSSTSAHH SHEQH (SEQ ID NO:3). The expressed protein is a transmembrane protein, having a transmembrane portion, a cytoplasmic portion and an extracellular portion, which includes the EGF portion that is proteolytically released upon cellular stimuli. The NRG4 compounds of the present invention comprise the portion of the expressed protein described above (SEQ ID NO:3) from amino acid numbers 4-50, which is in the extracellular portion of the expressed protein, as set forth below in SEQ ID NO:1:
DHEEPCGPSH KSFCLNGGLC YVIPTIPSPF CRCVENYTGA RCEEVFL (SEQ ID NO:1). For avoidance of doubt, the numbering herein of any amino acid modification in the context of NRG4 compounds of the present invention is based on the sequence set forth above in SEQ ID NO:1.

When used herein, the term "NRG4 compound" means a protein or peptide which comprises all or a part of the amino acid sequence of SEQ ID NO:1, or a variant or conjugate thereof. When used herein, the term "variant" refers to an amino acid sequence having one or more modifications to the amino acid sequence of the human protein. Such modifications include substitutions of one or more amino acids in the native human sequence with another natural or an unnatural amino acid and/or deletion or addition of one or more amino acids in the native human sequence. When used herein, the term "conjugate" refers to a protein or peptide which comprises all or a part of SEQ ID NO:1, or a variant thereof, and which is attached to a protein, peptide or other chemical moiety by covalent bond. Such attachments include, for example, IgG Fc regions, human albumin, glycine rich peptides or fatty acid moieties. In addition, unless expressly stated otherwise, when an NRG4 compound is described in an embodiment or recited in a claim herein, it should be understood that the compound may be in free or salt form.

The present invention provides NRG4 compounds which comprise the formula of SEQ ID NO:1, with one or more modifications thereto, and which have stronger HER4 affinity and HER4 binding-related activity than native human NRG4, and which are at least as selective in binding to the HER4 receptor over the HER3 receptor as native human NRG4. The affinity to and potency at the HER4 and HER3 receptors may be determined by techniques known in the art, including those described in the Examples below. In certain embodiments, the NRG4 compounds of the present invention have potency resulting from HER4 binding which is at least 50% of the maximal potency of the native human NRG1 EGF domain. In certain embodiments, the NRG4 compounds of the present invention have potency resulting from HER4 binding that is up to 90% of the maximal potency of the native human NRG1 EGF domain.

When used herein in describing certain NRG4 compounds, the term "no HER3 binding-related activity" means those compounds have no greater activity associated with HER3 binding than that of native NRG4 when tested using in vitro assays such as those described in the examples below.

The NRG4 compounds of the present invention comprise one or more modifications to the amino acid sequence set forth above in SEQ ID NO:1, including at least substitution of the D at position 1 with G (i.e., D1G). The D1G substitution was found to significantly improve binding to HER4 without negatively impacting selectivity over HER3, including in the context of NRG4 compounds that contain additional modifications to the wild type NRG4 amino acid sequence. Other amino acid modifications found to have beneficial effects—e.g., in terms of HER4 binding and/or selectivity relative to HER3—in combination with D1G in certain preferred embodiments of the present invention include modifications at one or more of positions 8, 22, 26, 35 and 44, including in particular one or more of the following: P8E, V22Q, I26F, E35A, E441H and E44K. Particularly preferred embodiments of NRG4 compounds of the present invention are triple variants having a combination of three amino acid substitutions selected from the following list: D1G/I26F/E44K; D1G/I26F/P8E; D1G/I26F/E44H; and D1G/V22Q/E44K. A most preferred embodiment of NRG4 compounds of the present invention comprises the following three amino acid substitutions: D1G/V22Q/E44K, as set forth in SEQ ID NO:4:

(SEQ ID NO: 4)
GHEEPCGPSHKSFCLNGGLCYQIPTIPSPFCRCVENYTGARCEKVFL

NRG4 compounds of the present invention may also include in certain embodiments one or more of the amino acids at the C- or N-terminal ends of the sequence set forth above in SEQ ID NO:1 that would be found in the full length expressed protein set forth in SEQ ID NO:3, provided that inclusion of such amino acids does not eliminate its stronger-than-native binding to and activity at HER4 or selectivity relative to HER3.

NRG4 compounds of the present invention may also comprise in certain embodiments one or more additional amino acids or other chemical moieties that are not found in the full length protein set forth in SEQ ID NO:3. For example, certain NRG4 compounds of the present invention are conjugated to a protein, glycine rich peptide and/or other chemical moiety by covalent bond. In certain embodiments, NRG4 compounds of the present invention comprise a glycine rich peptide comprising the sequence $(GGGGX_\lambda)_n$ wherein $X_\lambda$ is Q, A, E or S and wherein n=1-5 (SEQ ID NO:5). In certain embodiments, NRG4 compounds of the present invention comprise the sequence set forth in SEQ ID NO:5 wherein $X_\lambda$, is S and n=1 at the N-terminal end.

In certain embodiments, NRG4 compounds of the present invention comprise the formula: $X_0$GHEEPCGX$_8$SHKSFCLNGGLCYX$_{22}$IPTX$_{26}$PSPFCRCVX$_{35}$NYTG-ARCE X$_{44}$VFL; wherein: $X_0$ is selected from the group consisting of T, PT, MPT, S, GS, GGS, GGGS, and $(GGGGX_\lambda)_n$ wherein $X_\lambda$ is Q, A, E or S and n=1-5 (SEQ ID NO:5), or is absent; $X_8$ is E or P; $X_{22}$ is Q or V; $X_{26}$ is F or I; $X_{35}$ is E or A; and $X_{44}$ is H, K or E (SEQ ID NO:2).

In certain embodiments, $X_8$ is P; $X_{22}$ is V; $X_{26}$ is I; $X_{35}$ is E; and $X_{44}$ is E. In other embodiments, $X_8$ is E; $X_{22}$ is V; $X_{26}$ is I; $X_{35}$ is E; and $X_{44}$ is E. In other embodiments, $X_8$ is P; $X_{22}$ is Q; $X_{26}$ is I; $X_{35}$ is E; and $X_{44}$ is E. In other embodiments, $X_8$ is P; $X_{22}$ is V; $X_{26}$ is F; $X_{35}$ is E; and $X_{44}$ is E. In other embodiments, $X_8$ is P; $X_{22}$ is V; $X_{26}$ is I; $X_{35}$ is A; and $X_{44}$ is H or E. In other embodiments, $X_8$ is P; $X_{22}$ is V; $X_{26}$ is F; $X_{35}$ is E; and $X_{44}$ is K. In other embodiments, $X_8$ is P; $X_{22}$ is V; $X_{26}$ is F; $X_{35}$ is E; and $X_{44}$ is H. In other embodiments, $X_8$ is E; $X_{22}$ is V; $X_{26}$ is F; $X_{35}$ is E; and $X_{44}$ is E. In preferred embodiments, $X_8$ is P; $X_{22}$ is Q; $X_{26}$ is I; $X_{35}$ is E; and $X_{44}$ is K.

In certain embodiments, NRG4 compounds of the present invention comprise an IgG Fc region. As used herein, the term "IgG Fc region" refers to the constant region of a human IgG antibody fragment. In particular, the Fc region includes the CH2 and CH3 constant region domains of the antibody, and may also include some or all of the hinge region. The IgG Fc regions comprised in certain NRG4 compounds of the present invention may comprise fragments of the constant regions from either one heavy chain of an IgG antibody or two heavy chains, which are associated with one another through non-covalent interactions and disulfide bonds. When used herein, the term IgG Fc region also includes versions of such antibody fragments which have been modified, elongated and/or truncated, for example, to alter properties or characteristics of the NRG4 compound, such as its potency and/or pharmacokinetics. The human IgG Fc regions in certain embodiments of the present invention may also have some or all of the hinge region removed in order to simplify disulfide mediated Fc dimerization. The IgG Fc regions in certain embodiments of the present invention comprise dimers of two heavy chains having different amino acid sequences, which may be prepared by techniques known in the art. See, e.g., Lewis S M, et al. NAT. BIOTECHNOL. 32(2):191-8 (2014); Carter, J. IMMUNOL. METHODS, 248(1-2):7-15 (2001); Ridgway, J. B. et al. PROTEIN ENG. 9(7):617-2 (1996).

One preferred IgG Fc region is a dimer of the following two amino acid chains:

(SEQ ID NO: 6)
ECPPCPAPPVAGPSVFLFPPKPKDTLMISRTPEVTCVVVDVSHEDPEVQ

FNWYVDGVEVHNAKTKPREEQFNSTFRVVSVLTVVHQDWLNGKEYKCKV

SNKGLPAPIEKTISKTKGQPREPQVYTLPPSREEMTKNQVSLWCLVKGF

YPSDIAVEWESNGQPENNYKTTPPVLDSDGSFFLYSKLTVDKSRWQQGN

VFSCSVMHEALHNHYTQKSLSLSPG;
and (SEQ ID NO: 7)
ECPPCPAPPVAGPSVFLFPPKPKDTLMISRTPEVTCVVVDVSHEDPEVQ

FNWYVDGVEVHNAKTKPREEQFNSTFRVVSVLTVVHQDWLNGKEYKCKV

SNKGLPAPIEKTISKTKGQPREPQVYTLPPSREEMTKNQVSLSCAVKGF

YPSDIAVEWESNGQPENNYKTTPPVLDSDGSFFLVSKLTVDKSRWQQGN

VFSCSVMHEALHNHYTQKSLSLSPG.

Another preferred IgG Fc region is a dimer of the following two amino acid chains:

(SEQ ID NO: 8)
ECPPCPAPPVAGPSVFLFPPKPKDTLMASRTPEVTCVVVDVSHEDPEVQ

FNWYVDGVEVHNAKTKPREEQFNSTFRVVSVLTVVHQDWLNGKEYKCKV

SNKGLPAPIEKTISKTKGQPREPQVYTLPPSREEMTKNQVSLWCLVKGF

YPSDIAVEWESNGQPENNYKTTPPVLDSDGSFFLYSKLTVDKSRWQQGN

VFSCSVMHEALHNAYTQKSLSLSPG;
and (SEQ ID NO: 9)
ECPPCPAPPVAGPSVFLFPPKPKDTLMASRTPEVTCVVVDVSHEDPEVQ

FNWYVDGVEVHNAKTKPREEQFNSTFRVVSVLTVVHQDWLNGKEYKCKV

SNKGLPAPIEKTISKTKGQPREPQVYTLPPSREEMTKNQVSLSCAVKGF

YPSDIAVEWESNGQPENNYKTTPPVLDSDGSFFLVSKLTVDKSRWQQGN

VFSCSVMHEALHNAYTQKSLSLSPG.

In certain embodiments wherein NRG4 compounds of the present invention comprise an IgG Fc region, the IgG Fc region is attached by way of a linker. In certain embodiments the linker is a peptide linker comprising the sequence set forth above in SEQ ID NO:5 wherein $X_\lambda$ is Q, A, E or S and n=1-5. In certain embodiments, the linker comprises the sequence of SEQ ID NO:5 wherein $X_\lambda$ is S and n is 3. In certain embodiments wherein NRG4 compounds of the present invention comprise an IgG Fc region attached by way of a peptide linker, the N-terminal residue of the peptide linker is directly fused to the C-terminal residue of one chain of the IgG Fc region and the N-terminal residue of the NRG4 agonist is directly fused to the C-terminal residue of the peptide linker.

The inclusion of IgG Fc regions in certain NRG4 compounds of the present invention may have advantages with respect to production and/or administration. With respect to production, such compounds may be produced rapidly using biological expression techniques known in the art, such as those described in the examples below. Rapid production using such techniques provides efficiency in all phases of research and development, including in particular in producing NRG4 variants for screening for binding and/or activity. With respect to administration, NRG4 compounds which comprise IgG Fc regions may have prolonged pharmacokinetic profiles, including serum exposures as long as about 14 days.

Despite those advantages, however, it has also been discovered that prolonged exposure to NRG4, including serum exposures of greater than about 8 days, may create cardiac toxicity risks, as noted in the examples below. It has also been found that the toxicity risk may be attenuated, although not eliminated in all species, by preparing compounds (e.g., through the use of modified Fc regions) with somewhat shorter pharmacokinetic half-lives, including serum exposures of about 8 days.

It has also been discovered that providing shorter-term exposure to NRG4 compounds, as compared to the 8-14 day exposure durations described above, is capable of providing sufficient and sustained efficacy without the cardiac toxicity risks of NRG4 compounds described in the paragraphs above. Examples of such exposure durations are from about 1 to about 7 days, preferably 2, 3 or 4 days. Thus, in certain embodiments, the present invention provides a method of treating or preventing HFrEF wherein an NRG4 compound is administered in an amount sufficient to provide therapeutically effective serum concentrations for about 24 to about 168 hours. In certain embodiments, the NRG4 compound is administered in an amount sufficient to provide therapeutically effective serum concentrations for about 24 to about 96 hours. In certain embodiments, the NRG4 compound is administered in an amount sufficient to provide therapeutically effective serum concentrations for about 24 hours. In certain embodiments, the NRG4 compound is administered in an amount sufficient to provide therapeutically effective serum concentrations for about 48 hours. In certain embodiments, the NRG4 compound is administered in an amount sufficient to provide therapeutically effective serum concentrations for about 72 hours. In certain embodiments, the NRG4 compound is administered in an amount sufficient to provide therapeutically effective serum concentrations for about 96 hours.

The exposure durations described in the paragraph above may be achieved either through providing single bolus injections of NRG4 compounds with pharmacokinetic profiles that allow for serum exposures for the periods of time described in the above paragraph, or through the continuous administration (e.g., through the use of a pump) of a rapid-clearing NRG4 compound for the periods of time described in the paragraph above.

When used herein, the term "sustained efficacy" refers to heart failure-related improvements that extend beyond the period of time during which the NRG4 compound is administered. For example, in certain embodiments wherein an NRG4 compound is administered in an amount sufficient to provide therapeutically effective serum concentrations for 72 hours, in certain embodiments the efficacy of such a treatment regimen may be sustained for a period of time ranging from about 6 days (~2× the duration of administration) to about 4 months (~30× the duration of administration). The duration of efficacy (i.e., the amount of time for which clinical benefits are seen) relative to the duration of administration (i.e., the amount of time for which therapeutically effective serum concentrations are provided) is identified in certain embodiments herein as the "efficacy:administration ratio." In certain embodiments, the efficacy:administration ratio ranges from about 2 to about 50. In certain embodiments, the efficacy:administration ratio ranges from about 20 to about 45. In certain embodiments, the efficacy:administration ratio is about 22, about 30, or about 45.

Such sustained efficacy allows for relatively infrequent administration of the NRG4 compound in an amount sufficient to provide therapeutically effective serum concentrations for the desired period of time. In certain embodiments, NRG4 compounds are administered once every six months. In certain embodiments, NRG4 compounds are administered no more frequently than once weekly. In other embodiments, NRG4 compounds are administered bi-monthly. In other embodiments, NRG4 compounds are administered once monthly. In certain preferred embodiments, NRG4 compounds are administered once quarterly. In other preferred embodiments, NRG4 compounds are administered once every six months.

As used herein, the term "treating" or "to treat" includes restraining, slowing, stopping, or reversing the progression or severity of an existing symptom or disorder. Treatment of heart failure or HFrEF according to the present invention may be reflected in one or more of a variety of measures relevant to heart failure, including, for example: increases in left ventricular ejection fraction (LVEF), increases in left ventricular cavity volume at end-systole (LVESV), reductions in left ventricular end-diastolic pressure (LVEDP), reductions in the risk of CV death and/or heart failure hospitalization, reductions in the risk of total mortality, reductions in the risk of myocardial infarction (MI), reductions in the risk of stroke, reductions in the risk of need for left ventricular assist device (LVAD) implantation and/or cardiac transplant, improvement in symptoms and physical limitations of heart failure and/or improvement in quality of life (QoL). Certain benefits of treatment according to embodiments of the present invention may be achieved after treatment for at least 1 month. Certain benefits of treatment according to embodiments of the present invention may be achieved after treatment for at least 6 months. Certain benefits of treatment according to embodiments of the present invention may be achieved after treatment for at least 1 year.

In certain embodiments, administration of NRG4 compounds according to the present invention results in a significant improvement in LVEF. In certain embodiments, administration of NRG4 compounds according to the present invention results in at least a 5% improvement in LVEF. In certain embodiments, administration of NRG4 compounds according to the present invention results in at least a 5% improvement in LVEF after 6 months of treatment. In certain embodiments, administration of NRG4 compounds according to the present invention results in at least a 5% improvement in LVEF after 1 year of treatment. In certain embodiments, administration of NRG4 compounds according to the present invention results in at least a 5% improvement in LVESV after 1 year of treatment. In certain embodiments, administration of NRG4 compounds according to the present invention results in significant reductions in LVEDP after 1 year of treatment. In certain embodiments, administration of NRG4 compounds according to the present invention results in a significant reduction in global longitudinal strain (GLS). In certain embodiments, administration of NRG4 compounds according to the present invention results in at least a 3.5% reduction in GLS. In certain embodiments, administration of NRG4 compounds of the present invention results in at least a 15% reduction in risk of CV death and/or HF hospitalization. In certain embodiments, administration of NRG4 compounds of the present invention results in a significant reduction in the risk of one or more of total mortality, MI, stroke, LVAD implantation or cardiac transplant. In certain embodiments, administration of NRG4 compounds of the present invention results in a significant improvement in symptoms and physical limitations of heart failure and/or QoL.

In addition, as noted above, administration of NRG4 compounds according to certain embodiments of the presentation is capable of providing improvements in heart failure-related measures, such as those described above, without increasing safety risks. Thus, in preferred embodiments, administration of NRG4 compounds according to the present invention results in no increases in safety risks such as increased hypotension; worsened renal function; electrolyte imbalances; liver dysfunction; incidence of tumors or persistent hypospermia.

When used herein, the term "therapeutically effective amount" refers to the amount or dose of NRG4 compound which provides the desired effect in the patient. In the case of NRG4 compounds with extended pharmacokinetic profiles, such a dose may be the amount given upon single or multiple dose administration. In the case of more rapid acting compounds administered over a period of time, such as a 24-96 hour infusion as described above, the dose or amount may be expressed as the total mass of the NRG4 compound administered during that period of time, e.g., total mg, or rate at which the NRG4 compound is administered during that time, e.g., mg/min, or the plasma concentration of the NRG4 compound during the period of administration. Determining an effective amount can be readily accomplished by persons of skill in the art through the use of known techniques and by observing results obtained under analogous circumstances. In certain embodiments, dosages for once-quarterly administration may fall within the range of dosages sufficient to provide plasma concentrations from about 3 to about 100 nM for the period of administration.

Administration of NRG4 compounds according to the present invention is typically parenteral, e.g., intravenous (IV), subcutaneous (SC) or intraperitoneal (IP). Thus, in certain embodiments of the present invention, NRG4 compounds are administered intravenously. In other embodiments of the present invention, NRG4 compounds are administered intraperitoneally. In other embodiments, NRG4 compounds are administered subcutaneously.

In order to control duration of exposure for optimized and sustained efficacy with sufficient margin to cardiac toxicity, parenteral administration of NRG4 compounds is preferably by continuous or intermittent infusion. For example, many types of infusion pumps are used to infuse a broad range of medications and such pumps may be used in administering NRG4 compounds according to the present invention. More recently, patch pumps have been developed which are smaller than traditional devices and which attach directly to the patient's skin, resulting in minimal interference with patients' day-to-day activities. Thus, in certain embodiments, NRG4 compounds are administered by infusion pump or patch pump. Preferably, NRG4 compounds are administered by patch pump.

The present invention also encompasses novel intermediates and processes useful for the production of NRG4 compounds of the present invention. The intermediates and NRG4 compounds of the present invention may be prepared by a variety of procedures known in the art, including processes using chemical synthesis or biological expression, such as those described in the Examples below.

With respect to chemical synthesis, the specific synthetic steps for each of the routes described may be combined in different ways to prepare NRG4 compounds of the present invention. The reagents and starting materials are readily available to one of ordinary skill in the art.

With respect to biological expression, the compounds will be expressed in a host cell after the sequences have been operably linked to an expression control sequence. The compounds may readily be produced in mammalian cells such as CHO, NSO, HEK293, BHK, or COS cells; in bacterial cells such as *E. coli, Bacillus subtilis*, or *Pseudomonas fluorescens*; in insect cells, or in fungal or yeast cells, which are cultured using techniques known in the art. The vectors containing the polynucleotide sequences of interest can be transferred into the host cell by well-known methods, which vary depending on the type of cellular host. Various methods of protein purification may be employed and such methods are known in the art.

As noted above, all HF patients, even those who are mildly symptomatic are at high risk of dying. Thus, when used herein, references to a "patient in need" of a treatment for heart failure (HF) may refer to a broad range of individuals having HF, including those with a broad range disease severity as described below. The New York Heart Association (NYHA) has provided a classification scheme for the degree or severity of HF, as summarized below in Table 1:

TABLE 1

| NYHA Class | Symptoms |
|---|---|
| I | No limitation of physical activity. Ordinary physical activity does not cause undue fatigue, palpitation, dyspnea (shortness of breath). |
| II | Slight limitation of physical activity. Comfortable at rest. Ordinary physical activity results in fatigue, palpitation, dyspnea (shortness of breath). |
| III | Marked limitation of physical activity. Comfortable at rest. Less than ordinary activity causes fatigue, palpitation, or dyspnea. |
| IV | Unable to carry on any physical activity without discomfort. Symptoms of heart failure at rest. If any physical activity is undertaken, discomfort increases. |

In certain embodiments, the patient in need is in heart failure NYHA Class II-IV. In certain embodiments, the patient in need is in heart failure NYHA Class II. In certain embodiments, the patient in need is in heart failure NYHA Class III. In certain embodiments, the patient in need is in heart failure NYHA Class IV. In certain embodiments, the patient in need is in heart failure NYHA Class II-III.

As noted above, existing therapeutic treatment options for heart failure, including current standard of care, improve symptoms and slow down disease progression through hemodynamic mechanisms—e.g., reducing blood pressure, heart rate and/or plasma volume—to reduce the workload of the failing heart. The NRG4 compounds of the present invention, by contrast, achieve their effects through a different mechanism of action, namely, selective HER4 binding and the activity resulting therefrom, which directly improves cardiomyocyte survival and cell metabolism and promotes myocardial regeneration. Due to these different mechanisms of action, NRG4 compounds of the present invention can be administered on top of existing SoC without titration or monitoring. Thus, in certain embodiments, NRG4 compounds of the present invention may be administered in combination with one or more additional treatments for heart failure. In certain embodiments, the one or more additional treatments for heart failure are selected from the group consisting of beta blockers, ACE inhibitors, ARBs, MRAs, diuretics, ivabradine and sacubitril/valsartan (ENTRESTO®). In certain embodiments, NRG4 compounds of the present invention may be administered in combination with SGLT2 inhibitors or sGC activators.

The NRG4 compounds of the present invention may also have utility in treatment of other diseases or conditions, including but not limited to heart failure with preserved ejection fraction (HFpEF), other heart related disorders or conditions, Parkinson's disease, Alzheimer's disease, irritable bowel syndrome, skeletal disorders, kidney disease, diabetes, metabolic disease, nonalcoholic fatty liver disease (NAFLD) and nonalcoholic steatohepatitis (NASH).

Additional embodiments are described below:

An NRG4 compound comprising modification of the D residue at position 1 to a G residue and up to five additional modifications as compared to the amino acid sequence of human NRG4 (SEQ ID NO:1).

The NRG4 compound of the preceding embodiment having no more than 4 additional modifications. In an embodiment, the NRG4 compound has no more than 3 additional modifications. In an embodiment, the NRG4 compound has no more than 2 additional modifications.

The NRG4 compound of any of the above-described embodiments wherein the compound includes at least one modification at a position selected from the group consisting of 8, 22, 26, 35 and 44.

A compound comprising the formula: $X_0$GHEEPCGX$_8$SHKSFCLNGGLCYX$_{22}$IPTX$_{26}$PSPFCR-CVX$_{35}$NYTGARCE X$_{44}$VFL; wherein: $X_0$ is selected from the group consisting of T, PT, MPT, S, GS, GGS, GGGS, and (GGGGX$_\lambda$)$_n$ wherein X$_\lambda$ is Q, A, E or S and n=1-5 (SEQ ID NO:5), or is absent; X$_8$ is E or P; X$_{22}$ is Q or V; X$_{26}$ is F or I; X$_{35}$ is E or A; and X$_{44}$ is H, K or E (SEQ ID NO:2).

The compound of the above embodiment, wherein X$_8$ is P; X$_{22}$ is V; X$_{26}$ is I; X$_{35}$ is E; and X$_{44}$ is E.

The compound of any of the above-described embodiments, wherein X$_8$ is E; X$_{22}$ is V; X$_{26}$ is I; X$_{35}$ is E; and X$_{44}$ is E.

The compound of any of the above-described embodiments, wherein X$_8$ is P; X$_{22}$ is Q; X$_{26}$ is I; X$_{35}$ is E; and X$_{44}$ is E.

The compound of any of the above-described embodiments, wherein X$_8$ is P; X$_{22}$ is V; X$_{26}$ is F; X$_{35}$ is E; and X$_{44}$ is E.

The compound of any of the above-described embodiments, wherein X$_8$ is P; X$_{22}$ is V; X$_{26}$ is I; X$_{35}$ is A; and X$_{44}$ is H or E.

The compound of any of the above-described embodiments, wherein X$_8$ is P; X$_{22}$ is V; X$_{26}$ is F; X$_{35}$ is E; and X$_{44}$ is K.

The compound of any of the above-described embodiments, wherein X$_8$ is P; X$_{22}$ is V; X$_{26}$ is F; X$_{35}$ is E; and X$_{44}$ is H.

The compound of any of the above-described embodiments, wherein X$_8$ is E; X$_{22}$ is V; X$_{26}$ is F; X$_{35}$ is E; and X$_{44}$ is E.

The compound of any of the above-described embodiments, wherein X$_8$ is P; X$_{22}$ is Q; X$_{26}$ is I; X$_{35}$ is E; and X$_{44}$ is K.

The compound of the preceding embodiment wherein X$_0$ is SEQ ID NO:5 wherein X$_\lambda$ is S and n=1.

A compound comprising the amino acid sequence of SEQ ID NO:4.

A compound comprising the amino acid sequence of SEQ ID NO:10.

A compound comprising the amino acid sequence of SEQ ID NO:11.

A compound comprising the amino acid sequence of SEQ ID NO:12.

A compound comprising the amino acid sequence of SEQ ID NO:13.

A compound comprising the amino acid sequence of SEQ ID NO:14.

A compound comprising the amino acid sequence of SEQ ID NO:15.

A compound comprising the amino acid sequence of SEQ ID NO:16.

A compound comprising the amino acid sequence of SEQ ID NO:17.

A compound comprising the amino acid sequence of SEQ ID NO:18.

A compound comprising the amino acid sequence of SEQ ID NO:19.

A compound consisting of the amino acid sequence of SEQ ID NO:18.

The compound of any of the preceding embodiments wherein the compound is attached to a protein, peptide or other chemical moiety by covalent bond. The compound of any of the preceding embodiments wherein the compound is attached to one or more of an IgG Fc region, human albumin, a glycine rich peptide or a fatty acid moiety. The compound of any of the preceding embodiments wherein the compound is attached to an IgG Fc region. The compound of the preceding embodiment wherein the IgG Fc region comprises a dimer of either SEQ ID NO:6 and SEQ ID NO:7 or SEQ ID NO:8 and SEQ ID NO:9. The compound of the preceding embodiments wherein X$_0$ is SEQ ID NO:5 wherein X$_\lambda$ is S and n=3.

The compound of any of the above embodiments, wherein the compound has HER4 binding-related activity which is greater than that of native human NRG4.

The compound of any of the above embodiments, wherein the compound has HER4 binding-related activity which is at least 50% that of the maximal activity of native human NRG1.

The compound of any of the above embodiments, wherein the compound has HER4 binding-related activity which is at least 70% that of the maximal activity of native human NRG1.

The compound of any of the above embodiments, wherein the compound has HER4 binding-related activity which is at least 90% that of the maximal activity of native human NRG1.

The compound of any of the above embodiments, wherein the compound has no HER3 binding-related activity.

A pharmaceutical composition comprising the compound of any of the above embodiments.

A pump device comprising the compound of any of the above embodiments.

A method of treating or preventing HF in a patient in need thereof, comprising administering to the patient a therapeutically effective amount of an NRG4 compound. In an embodiment, the NRG4 compound is a compound of any of the above embodiments.

An NRG4 compound for use in treating or preventing HFrEF. In an embodiment, the NRG4 compound is a compound of any of the above embodiments.

An NRG4 compound for use in the manufacture of a medicament for the treatment or prevention of HFrEF. In an embodiment, the NRG4 compound is a compound of any of the above embodiments.

In an embodiment, the compound is administered for 24-168 hours. In an embodiment, the compound is administered for 24-96 hours. In an embodiment, the compound is administered for 24, 48, 72 or 96 hours. In an embodiment, the compound is administered for 96 hours.

In an embodiment, the compound is administered no more frequently than once monthly. In an embodiment, the compound is administered no more frequently than once quarterly (Q3M). In an embodiment, the compound is administered Q3M. In an embodiment, the compound is administered Q3M for 96 hours. In an embodiment, the compound is administered once every six months.

In an embodiment, the efficacy:administration ratio is from about 2 to about 50. In an embodiment, the efficacy:administration ratio is from about 20 to about 45. In an embodiment, the efficacy:administration ratio is about 22, about 30, or about 45.

In an embodiment, treatment is continued for at least 6 months.

In an embodiment, treatment is continued for at least 1 year.

In an embodiment, the compound results in a significant increase in LVEF. In an embodiment, the compound results in at least a 5% increase in LVEF. In an embodiment, the compound results in a 5% improvement in LVEF after 1 year of treatment.

In an embodiment, the compound results in a significant increase in LVESV. In an embodiment, the compound results in a 5% improvement in LVESV. In an embodiment, the compound results in a 5% improvement in LVESV after 1 year of treatment.

In an embodiment, the compound results in a significant reduction in LVEDP. In an embodiment, the compound results in a significant reduction in LVEDP after 1 year of treatment.

In an embodiment, the compound results in a significant reduction in global longitudinal strain (GLS). In an embodiment, the compound results in at least a 3.5% reduction in GLS.

In an embodiment, the compound results in a significant improvement in LVEDV.

In an embodiment, the compound results in a significant reduction in risk of CV death and/or HF hospitalization.

In an embodiment, the compound results in at least a 15% reduction in risk of CV death.

In an embodiment, the compound results in at least a 15% reduction in risk of HF hospitalization.

In an embodiment, the compound results in a significant reduction in the risk of one or more of total mortality, MI, stroke, LVAD implantation or cardiac transplant.

In an embodiment, the compound results in a significant improvement in symptoms and physical limitations of heart failure and/or QoL.

In an embodiment, the compound results in no: increased hypotension; worsened renal function; electrolyte imbalances; liver dysfunction; incidence of tumors or persistent hypospermia.

In an embodiment, the compound is administered parenterally.

In an embodiment, the compound is administered intravenously, subcutaneously or intraperitoneally.

In an embodiment, the compound is administered by infusion pump.

In an embodiment, the compound is administered by patch pump.

In an embodiment, the therapeutically effective amount is an amount of the compound that provides serum concentrations of about 3 to about 100 nM.

In an embodiment, the compound is administered to a patient in heart failure NYHA Class II-IV.

In an embodiment, the compound is administered to a patient in heart failure NYHA Class II-III.

In an embodiment, the compound is administered in simultaneous or sequential combination with one or more additional treatments for heart failure. In an embodiment, the one or more additional treatments for heart failure are selected from the group consisting of beta blockers, ACE inhibitors, ARBs, MRAs, diuretics, ivabradine and sacubitril/valsartan (ENTRESTO®). In an embodiment, the compound is administered in simultaneous or sequential combination with an SGLT2 inhibitor and/or an sGC activator.

In an embodiment, the NRG4 compound administered is an NRG4 compound of the present invention.

The invention is further illustrated by the following examples, which are not to be construed as limiting.

PREPARATION OF EXAMPLE COMPOUNDS

Examples of NRG4 compounds of the present invention are described below in Table 2.

TABLE 2

Components of Example NRG4 compounds. Complete amino acid sequences for the Example compounds, excluding any IgG Fc region sequences, are provided at the SEQ ID NOs listed in the fourth column. Examples 1-8 and 10-11 further comprise IgG Fc regions. The IgG Fc regions of Examples 1-8 and 10 comprise a dimer of SEQ ID NO: 6 and SEQ ID NO: 7 wherein the N terminal amino acid of the sequence identified in the third column of the table above is fused to the C-terminal amino acid of SEQ ID NO: 7. The IgG Fc region of Example 11 comprises a dimer of SEQ ID NO: 8 and SEQ ID NO: 9 wherein the N terminal amino acid of the sequence identified in the third column of the table above is fused to the C-terminal amino acid of SEQ ID NO: 9.

| Example | NRG4 Modifications | N-terminal AAs/Linker | Sequence ID |
|---|---|---|---|
| 1 | D1G | SEQ ID NO: 5 wherein $X_\lambda$ is S and n is 3 | SEQ ID NO: 10 |
| 2 | D1G/P8E | SEQ ID NO: 5 wherein $X_\lambda$ is S and n is 3 | SEQ ID NO: 11 |
| 3 | D1G/V22Q | SEQ ID NO: 5 wherein $X_\lambda$ is S and n is 3 | SEQ ID NO: 12 |
| 4 | D1G/I26F | SEQ ID NO: 5 wherein $X_\lambda$ is S and n is 3 | SEQ ID NO: 13 |
| 5 | D1G/E35A | SEQ ID NO: 5 wherein $X_\lambda$ is S and n is 3 | SEQ ID NO: 14 |
| 6 | D1G/I26F/E44K | SEQ ID NO: 5 wherein $X_\lambda$ is S and n is 3 | SEQ ID NO: 15 |
| 7 | D1G/I26F/E44H | SEQ ID NO: 5 wherein $X_\lambda$ is S and n is 3 | SEQ ID NO: 16 |
| 8 | D1G/I26F/P8E | SEQ ID NO: 5 wherein $X_\lambda$ is S and n is 3 | SEQ ID NO: 17 |
| 9 | D1G/V22Q/E44K | SEQ ID NO: 5 wherein $X_\lambda$ is S and n is 1 | SEQ ID NO: 18 |
| 10 | D1G/V22Q/E44K | SEQ ID NO: 5 wherein $X_\lambda$ is S and n is 3 | SEQ ID NO: 19 |
| 11 | D1G/V22Q/E44K | SEQ ID NO: 5 wherein $X_\lambda$ is S and n is 3 | SEQ ID NO: 19 |

Biological Expression

Examples of NRG4 compounds comprising Fc regions are produced in a mammalian cell expression system using a CHO GSKO cell line. The GS gene knockout enables tightened selection stringency by eliminating endogenous GS background activity which can allow the survival of low- or non-productive cells under selection conditions. Genes coding for the Fc fusion knob chain and hole chain of the present invention may be sub-cloned into individual glutamine synthetase (GS)-containing expression plasmids for co-transfection or both chains may be sub-cloned into a single GS-containing expression plasmid. Alternatively, different ratios of knob chain and hole chain may be combined into a single GS-containing expression if there is need to alter relative expression levels of either chain. The cDNA sequence encoding the knob chain or hole chain is fused in frame with the coding sequence of a signal peptide, which may be the murine kappa leader sequence, to enhance secretion of the desired product into the cell culture medium. The expression is driven by the viral cytomegalovirus (CMV) promoter.

CHO GSKO cells may be transiently or stably transfected. For stable transfection, CHO GSKO cells are transfected using electroporation and the appropriate amount of recombinant knob chain and hole chain expression plasmids, and the transfected cells are maintained in suspension culture, at the adequate cell density. Selection of the transfected cells is accomplished by growth in glutamine-free, 25 µM methionine sulfoximine (MSX)-containing serum-free medium and incubated at 32-37° C. and 5-7% CO2. Fc fusions are secreted into the media from the CHO cells.

Proteins are purified using either: (1) Protein A affinity chromatography followed by cation exchange or hydrophobic interaction chromatography (or other suitable methods); or (2) multimodal chromatography followed by hydrophobic interaction chromatography (or other suitable methods).

For purification starting with protein A chromatography, proteins from harvested media are captured onto Mab Select SuRe Protein A resin (GE Healthcare). The resin is then briefly washed with a running buffer, such as a phosphate buffered saline (PBS), pH 7.4 or a running buffer containing Tris, to remove non-specifically bound material. The protein is then eluted from the resin with a low pH solution, such as 20 mM acetic acid/5 mM citric acid. Fractions containing Fc fusion are pooled. The pH can be increased as needed by adding a base such as 0.1 M Tris pH 8.0. At this stage Fc fusions may be used to screen binding/activity, or if desired may be further purified by hydrophobic interaction chromatography using resins such as Phenyl Sepharose HP. Fc fusions can be eluted from the Phenyl Sepharose HP column using a 500 mM to 0 mM gradient of sodium sulfate in 10 mM sodium phosphate, pH 7 over 10 column volumes. The Fc fusions may be further purified by size exclusion chromatography by using a Superdex 200 column (GE Healthcare) with isocratic elution in PBS, pH 7.4 or buffer exchanged into the desired buffer. Examples 1-8 and 10 are purified in this manner.

For purification starting with multimodal chromatography, proteins from harvested media are captured onto CaptoMMC resin (GE Healthcare). The resin is then briefly washed with 100 mM citrate, pH 5.0 ("A" buffer) prior to an 80%/20% wash of "A" buffer and 25 mM sodium phosphate, 1 M sodium chloride, pH 7.5 ("B" buffer). The desired protein is then eluted from the resin at 70% "B" buffer. Fc fusions may be further purified by hydrophobic interaction chromatography using resins such as Phenyl Sepharose HP (GE Healthcare). Fc fusions can be eluted from the Phenyl Sepharose HP column using a 800 mM to 0 mM linear gradient of sodium sulfate in 20 mM Tris, pH 8. The Fc fusions may be further purified by ion exchange chromatography by using a Q Sepharose column (GE Healthcare). Fc fusions can be eluted from the column using a 0 M to 1 M sodium chloride gradient in 20 mM Tris, pH 8. Fractions are pooled and buffer exchanged into the desired buffer for storage. Example 11 is purified in this manner.

Chemical Synthesis

NRG4 compounds of the present invention which are peptides that do not comprise IgG Fc regions (e.g., Example 9 in Table 2 above) may also be generated by solid-phase peptide synthesis using Fmoc/t-Bu strategy. The peptides are synthesized on a SymphonyX automated peptide synthesizer (PTI Protein Technologies Inc.).

Fmoc-L-Leu-Wang resin (0.3-0.8 mmole/gram, 200-400 mesh, Chem-Impex) is used for synthesizing the peptide. Fmoc deprotection is carried out using a 20% v/v solution of piperidine in DMF. Amino acid couplings are performed using 10 equivalents of Fmoc-amino acid, 0.9 M diisopropylcarbodiimide (DIC) and 0.9 M Oxyma (1:1:1 molar ratio) in DMF for 2 h at 25° C. Washing steps are performed with DMF and are included after every coupling and deprotection step. Additional details are provided below in Table 3.

TABLE 3

| Fmoc-deprotection and coupling protocol. | | | |
| --- | --- | --- | --- |
| Step | Solvent/Operation | Mixing Time | Repetitions |
| 1 | DMF | 00:01:00 | 2 |
| 2 | 25% Piperidine/DMF | 00:10:00 | 3 |
| 3 | DMF | 00:01:00 | 1 |
| 4 | DMF | 00:01:00 | 5 |
| 5 | Methylene Chloride | 00:01:00 | 1 |
| 6 | Methylene Chloride | 00:00:02 | 1 |
| 7 | Reagent (Amino Acid) | 00:00:01 | 1 |
| 8 | 0.9M Oxyma in DMF | 00:00:01 | 1 |
| 9 | 0.9M DIC in DCM | 03:00:00 | 1 |
| 10 | DMF | 00:01:00 | 3 |

All amino acids used in the main sequence are L amino acids: Fmoc-Ala-OH, Fmoc-Cys(Trt)-OH, Fmoc-Asp(Otbu)-OH, Fmoc-Glu(Otbu)-OH, Fmoc-Phe-OH, Fmoc-Gly-OH, Fmoc-His(Trt)-OH, Fmoc-Ile-OH, Fmoc-Lys(Boc)-OH, Fmoc-Leu-OH, Fmoc-Met-OH, Fmoc-Asn(Trt)-OH, Fmoc-Pro-OH, Fmoc-Gln(Trt)-OH, Fmoc-Arg(Pbf)-OH, Fmoc-Ser(tBu)-OH, Fmoc-Thr(tBu)-OH, Fmoc-Tyr(tBu)-OH, Fmoc-Val-OH, Fmoc-Trp(Boc)-OH.

After finishing the elongation of the peptide-resin described above, the final Fmoc group is removed and resin is washed with methylene chloride before subjecting the peptides to cleavage. 1.5 mL solution of water, triisopropylsilane, thioanisole, 1,2 ethanedithiol (1:1:1) added into 13 mL of trifluoroacetic acid (TFA) and the resultant cleavage cocktail is added to the resin and mixed for 2.5 h in a reaction syringe. TFA solution containing cleaved peptide is transferred into a 50 mL conical vial containing cold diethyl ether. Precipitated peptide solution is spun down to a thick pellet and ether is decanted. Ether precipitation is repeated twice to wash the residual cocktail before proceeding to refolding.

The crude peptide is dissolved in water and acetonitrile is added if necessary. The crude peptide concentration is adjusted to 2.5-3 mg/mL (200 mL) in acetonitrile and water. The sample is then subjected to refolding directly. Refolding buffer is prepared by adding oxidized glutathione and reduced glutathione at the ratios, GSSG:GSH (2 mM:1 mM)

in 0.1 M tris buffer, pH 8. Crude peptide solution is added into refolding buffer to the concentration of 0.13-0.15 mg/mL (diluted 20 fold) and the refolding mixture was kept at 4° C. without stirring. After 1 day, the refolding mixture is quenched by adding TFA up to 0.2% in order to bring the pH to 3.0. The quenched solution is then filtered and purified.

The peptide solution is loaded onto a HPLC column and then equilibrated with buffer A before triggering the gradient. Buffer A: 0.1% TFA in water; Buffer B: 100% acetonitrile. Gradient: 10% B to 25% B in 100 min. Flow rate: 18 mL/min; detection at 220 nm (Waters 2489 Detector). Column: Waters Symmetry Prep C18 column, 7 μm, 19×300 mm (Waters Part #WAT066245). Fractions auto triggered by UV and collected using Waters Fraction Collector III.

The pooled fractions containing the desired peptide are combined and lyophilized.

In Vitro Studies

HER4/NRG-Fc Binding Assay for Screening of NRG4 Variants for Improved Binding

A binding assay is utilized to perform high-throughput screening of NRG4 variant Fc fusion proteins to HER4 receptor, to identify affinity-driven variants with the potential to increase receptor activation and signaling. ELISA plates are coated with an anti-His tag antibody at 2 μg/ml in PBS to facilitate the standardized capture of a C-terminal His-tagged HER4 receptor extracellular domain (ECD) construct after blocking the plate with 1% BSA/PBS/0.1% Tween 20 (HER4 ECD at 5 μg/ml). Saturating amounts of unpurified NRG4-Fc variants in expression media (Starting at 10 μg/ml with serial dilutions in 1% BSA/PBS/0.1% Tween 20) are incubated with the captured receptor for 1 hour. After washing, bound variant NRG4-Fc is detected colorimetrically with an anti-human Fc-specific alkaline phosphatase secondary detection reagent to quantitate binding. Incubation times of variant binding to receptor or durations of the subsequent wash steps are varied to further identify binding variants driven by affinity on-rate and off-rate, respectively. This screening process identifies the D1G modification, as included in Example 1, as having high affinity and potential to increase receptor activation and signaling, as indicated in the data below in Table 4.

TABLE 4

Binding to HER4 extracellular domain.

| | Example 1 | | WT NRG1 | | WT NRG4 | |
|---|---|---|---|---|---|---|
| Dose # | dose (μg/mL) | O.D. 405 | dose (μg/mL) | O.D. 405 | dose (μg/mL) | O.D. 405 |
| 1 | 10.65 | 1.485 | 10 | 1.501 | 17 | 0.651 |
| 2 | 5.325 | 1.438 | 5 | 1.439 | 8.5 | 0.597 |
| 3 | 2.6625 | 1.4 | 2.5 | 1.399 | 4.25 | 0.485 |
| 4 | 1.33125 | 1.332 | 1.25 | 1.31 | 2.125 | 0.347 |
| 5 | 0.665625 | 1.217 | 0.625 | 1.27 | 1.0625 | 0.224 |
| 6 | 0.332813 | 1.081 | 0.3125 | 1.022 | 0.53125 | 0.154 |
| 7 | 0.166406 | 0.865 | 0.15625 | 0.8 | 0.265625 | 0.111 |
| 8 | 0.083203 | 0.607 | 0.078125 | 0.514 | 0.132813 | 0.088 |
| 9 | 0.041602 | 0.404 | 0.039063 | 0.316 | 0.066406 | 0.071 |
| 10 | 0.020801 | 0.235 | 0.019531 | 0.179 | 0.033203 | 0.07 |
| 11 | 0.0104 | 0.136 | 0.009766 | 0.114 | 0.016602 | 0.066 |
| 12 | 0.0052 | 0.096 | 0.004883 | 0.084 | 0.008301 | 0.066 |

As seen in Table 4, Example 1, which includes the D1G modification, has similar HER4 binding to WT NRG1 at similar doses, and significantly greater HER4 binding than WT NRG4 at similar doses in this study.

Generation of CHO Human and Rat HER2-4 and HER2-3 Cell Lines

A cell based assay utilizing CHO-K1 cells overexpressing human or rat HER receptors is used to determine activity of NRG4 compounds. CHO-K1 cells (ATCC) are grown in DMEM-F12 3:1 with 5% FBS with 20 mM HEPES, 40 μg/mL L-Proline, 1× antibiotics and were split 1:5 every 2-3 days with TripLE Express (Gibco). Cells are transfected with plasmid DNA encoding HER receptors in pairs (hHER2-3, hHER2-4, rHER2-3 and rHER2-4) with Fugene 6 (Promega) according to the manufacturer's instructions. HER2 is included, because this receptor does not bind ligand but is the preferred dimerization partner of the HER receptors for downstream signaling. Transfected cells are selected with Puromycin (12 ug/ml) and Hygromycin (1 mg/ml) for 3-4 weeks and clonal lines are obtained by limited dilution cloning into 96 well plates. Clonal lines are selected by appropriate gene expression of HER2, HER3 or HER4 by Taqman method. Lines with appropriate receptor expression are confirmed by NRG1 induced phospho-ERK 1/2 responses. Clones are grown up, harvested, aliquoted into cryovials and then frozen under liquid nitrogen for long-term storage.

Screening of Molecules by Human HER2-HER4 Mediated ERK 1/2 Phosphorylation In Vitro A phospho-ERK1/2 activity assay is used to determine potencies of NRG4 compounds. The potency of Examples 1-8 and 10 as compared to WT human NRG1 and/or human NRG4 are analyzed in studies measuring stimulation of human HER2-HER4 mediated ERK 1/2 phosphorylation. This assay comprises a CHO-K1 stable line expressing human HER2 and HER4. CHO-hHER2-hHER4 (clone 1H6) cells are routinely cultured in DMEM: F12(3:1), 5% FBS, 40 μg/mL L-Proline, 10 μg/mL puromycin and 1 mg/mL hygromycin at 37° C., 5% $CO_2$. Cells are washed twice with 1× PBS, dissociated with 0.05% trypsin/0.53 μM EDTA and collected by centrifugation at 300×g for 10 m. Cells are re-suspended in maintenance media. 20,000 cells/well, in 30 μL, are seeded into 384 well Poly-D-Lysine cell culture plates (Greiner, Cat No. 781946). Plates are covered with a manufacturer's lid and moved to a 37° C. tissue culture incubator at 5% $CO^2$, 80%+ humidity and allowed to adhere. After 24 h, media are removed from the plates and replaced with 30 μL serum-free starvation media (Low glucose DMEM with 0.1% BSA) using a Biomek FX liquid handler. Plates are returned to the incubator for 24 h.

hFcNRG4 variants, transiently expressed as 293F supernatants, are prepared in starvation media in a clear 384W plate (Greiner, cat no. 781185) as a 4 pt 1:8 serial dilution (dose range averaged between 250 pM to 140000 pM). Media are removed from the cell culture plates and the 30 uL/well prepared variants are stamped into the plates using a Biomek FX liquid handler. Plates are sealed with a foil seal and stimulated for 15 minutes at room temperature on an orbital shaker. Cells are then washed once with 50 uL cold PBS. 30 uL lysis buffer is added to the cells and oscillated for 10 m at RT on an orbital shaker.

Detection of phosphorylation of ERK 1/2 is performed with either an AlphaScreen SureFire phospho-ERK1/2 kit (T202/Y204) (Perkin Elmer, catalog no. TGRES) or an AlphaLISA® SureFire® Ultra™ p ERK1/2 assay kit together with the AlphaScreen Protein. A IgG Detection Kit (Protein-A) (PerkinElmer, catalogue no. 6760617). After lysis of the CHO-K1 cells, 4 μL lysate is transferred to a 384 W Alpha Proxiplate (Perkin Elmer, cat no, 6008280) with a 384 W Biomek FX. 4 uL positive and negative lysates (Perkin Elmer, TGRES-L) are added to available wells as controls. 5 uL/well acceptor mix (containing anti-phoso-Thr202/Tyr204 antibodies and Protein A conjugated acceptor beads) is added to the plate with a Forumlatrix Mantis. The plate is sealed, spun down for 1 min at 300×g and incubated for 2 hr at room temperature on an orbital shaker. 2 μL/well donor mix (containing strepavidin coated donor beads and biotinylated antibodies to a distal ERK1/2 epitope) is dispensed by Mantis. The plate is sealed, spun down for 1 min at 300×g and incubated for 2 hr at room temperature on an orbital shaker before reading on the Perkin Elmer Envision 2103 Multilabel Reader (HIS Alpha mode, excitation time: 40 ms, total measurement time: 130 ms).

Each sample is plotted against the parental hFcNRG4 dose response, included on every plate in replicate in XLFit. This data is plotted in GraphPad Prism with a four parameter fit, and EC50 potency values are extracted. Results are provided in Tables 5 and 6.

TABLE 5

Activity of Examples 1-5 as compared to
WT NRG4. Data for Examples 1-5 represent an average
of two replicates with standard deviations indicated.

| Sample | EC50 (nM) |
| --- | --- |
| WT NRG4 | 2.53 |
| Example 1 | 0.77 ± 0.16 |
| Example 2 | 2.77 ± 0.39 |
| Example 3 | 0.29 ± 0.01 |
| Example 4 | 0.53 ± 0.05 |
| Example 5 | 0.84 ± 0.27 |

As seen in the data in Table 5, consistent with its increased affinity to HER4, in this study the D1G modification also significantly increases activity at HER4 and HER2 as compared to wild type NRG4, including in examples which include additional amino acid modifications.

TABLE 6

Activity of Examples 6-8 and
10 as compared to WT NRG1 and NRG4.

| Sample | EC50 (nM) |
| --- | --- |
| WT NRG1 | 0.3192 |
| WT NRG4 | 1.2980 |
| Example 6 | 0.3947 |
| Example 7 | 0.5629 |
| Example 8 | 0.4033 |
| Example 10 | 0.2448 |

As seen in the data in Table 6, in this study Examples 6-8 and 10, each of which includes the D1G modification and additional modifications, show increased activity at HER4 and HER2 as compared to WT NRG4 and similar activity as compared to WT NRG1.

Human and Rat HER2-4 or HER2-3 Phospho-ERK 1/2 (Thr202/Tyr204) Assays for Testing of Purified Proteins A phospho-ERK1/2 activity assay is utilized with CHO-K1 cells overexpressing human or rat HER receptors to determine potencies and selectivity of purified NRG4 compounds. CHO-K1 cell lines expressing the human or rat HER receptors are cultured with selection medium (DMEM-F12 3:1 with 5% FBS with 20 mM HEPES, 40 μg/mL L-Proline, 1× antibiotics, 12 μg/mL puromycin, 1 mg/mL Hygromycin B). On Day-1 (the day before phospho-ERK1/2 assay), cells are washed once with PBS, detached with enzyme free cell dissociation solution (GIBCO cat #13151-014), and resuspended in plating medium (DMEM-F12 3:1 with 20 mM HEPES, 1× antibiotics, 0.2% FBS). Cells are plated in a 96-well Poly-D-Lysine coated plate (BD cat #354640) at 10,000 cells per 0.1 mL per well. Cells are cultured in a tissue culture incubator at 37° C. 5% CO2 overnight. On Day 1 (the day of pERK1/2 assay), plates are incubated at room temperature for 30 min. The culture media are removed followed by addition of 50 μL ligand at various concentrations diluted in PBS-20 mM HEPES-0.005% BSA. Native human NRG1 and NRG4 peptides are purchased from Reprokine (Tampa, FL). The stimulation time is 30 min (except for hHER2-4 1H6 line in which 15 min is used for stimulation). At the end of stimulation, ligands are removed and 70 μL Lysis buffer (made according to manufacturer's recipe, Perkin Elmer cat #ALSU-PERK-A10K) is added. Plates are incubated at room temperature for 10 min on plate shaker with 350 rpm agitation, then on ice for 1 hour without shaking. 30 μL of cell lysis is transferred to a 96-well white Optiplate (Perkin Elmer cat #6002290) for phospho-ERK1/2 assay. Briefly 7.5 μL acceptor beads are added to 30 μL lysis in Optiplate. The plate is covered with aluminum foil and incubated at room temperature for 1 hour on plate shaker with 350 rpm agitation. Then 7.5 μL donor beads are added and the plate is covered with aluminum foil and incubated at room temperature for 2 hours on plate shaker with 350 rpm agitation or at 4° C. for overnight (warm up plate at room temperature for 2 h before reading). Alpha signal data are obtained on an Envision instrument (Alpha Technology-compatible plate reader). Donor beads and acceptor beads are made according to assay protocol. The data shown are generated with either the AlphaScreen SureFire p-ERK1/2 (Thr202/Tyr204) assay kit (Cat #TGRES50k) or the AlphaLISA® SureFire® Ultra™ p-ERK 1/2 (Thr202/Tyr204) assay kit (Perkin Elmer cat #ALSU-PERK-A10K). The activity of the NRG1 peptide was similar in both types of assays. Raw data obtained from the Envision instrument is imported into GraphPad Prism software (version 7). The EC50 value is generated by a variable slope-four parameter dose response curve. The % of maximal NRG1 activity data are generated by expressing the average maximal raw data for the NRG4 compound over the average maximal raw data for the native human NRG1 per plate and multiplying by 100. Data are provided below in Tables 7-9. N values reflect number of independent assays run.

TABLE 7

Human HER2/HER4 Assay.

| Sample | EC50 (nM) | % Maximal NRG1 activity |
| --- | --- | --- |
| WT NRG1 | 0.67 ± 0.07 (N = 9) | 100 |
| WT NRG4 | 90.09 ± 33.21 (N = 8) | 75 ± 4 (N = 8) |
| Example 9 | 0.20 ± 0.01 (N = 11) | 91 ± 3 (N = 11) |
| Example 10 | 0.16 ± 0.02 (N = 8) | 82 ± 4 (N = 8) |
| Example 11 | 0.55 ± 0.11 (N = 5) | 79 ± 2 (N = 5) |

TABLE 8

Rat HER2/HER4 Assay.

| Sample | EC50 (nM) | % Maximal NRG1 activity |
| --- | --- | --- |
| WT NRG1 | 0.29 ± 0.05 (N = 4) | 100 |
| Example 9 | 0.17 ± 0.02 (N = 4) | 87 ± 4 (N = 4) |
| Example 10 | 0.12 ± 0.04 (N = 2) | 88 ± 7 (N = 2) |
| Example 11 | 0.17 ± 0.06 (N = 2) | 96 ± 2 (N = 2) |

As seen in Table 7, wild type human NRG1 peptide exhibits potent activity at the human HER4 and HER2 receptors while wild type human NRG4 peptide behaves as a weak partial agonist. Examples 9-11 exhibit potent activity with EC50 values slightly more potent than wild type human NRG1 and % maximal activities greater than wild type human NRG4 peptide and approaching that of human NRG1. As seen in Table 8, similar results are obtained at the rat HER4 HER2 receptors with slight increases in potency relative to human NRG1 and maximal activity approaching that of human NRG1. In conclusion, the examples shown of NRG4 compounds exhibit greater phospho-ERK1/2 activity at both human and rat HER4 HER2 receptors relative to native human NRG4 and approaching that of native human NRG1.

TABLE 9

Human and Rat HER2/HER3 Assay

| Sample | Human HER2/HER3 Assay EC50 (nM) | Rat HER2/HER3 Assay EC50 (nM) |
|---|---|---|
| WT NRG1 | 0.83 ± 0.20 (N = 6) | 32 ± 14 (N = 2) |
| WT NRG4 | No activity up to 1000 nM (N = 1) | nd |
| Example 9 | No activity up to 3000 nM (N = 6) | No activity up to 3000 nM (N = 4) |
| Example 10 | No activity up to 1000 nM (N = 3) | No activity up to 100 nM (N = 2) |
| Example 11 | No activity up to 1000 nM (N = 1) | No activity up to 1000 nM (N = 2) |

As seen in Table 9, wild type human NRG1 peptide exhibits potent activity at the human HER3 HER2 receptors while wild type human NRG4 peptide and all the Examples show no activity at this receptor pair demonstrating differential selectivity to the HER4 HER2 receptor pair. In conclusion, the examples of NRG4 compounds demonstrate no phospho-ERK1/2 activity at HER3 HER2 receptors thus showing maintenance of the HER4 and HER2 receptor selectivity of the wild type NRG4 peptide.

In Vivo Studies

Effects of Example 9 on Cardiac Function and Structure in Rat MI Model

Two nonclinical efficacy pharmacology studies are conducted in a rat model of heart failure with reduced ejection fraction (HFrEF) to study plasma concentration and duration of exposure for Example 9. Both studies measure effects on cardiac function and structure in male Sprague Dawley rats with surgically induced myocardial infarction.

Similar methodologies are used for both studies. Male Sprague Dawley rats with surgically induced myocardial infarction are purchased and anesthetized and positively ventilated throughout the procedure. An incision is made between the fourth and fifth ribs, revealing the heart. The left coronary artery is permanently ligated. The sham-operated animals undergo the same procedure except the silk suture is placed around the left coronary artery without being tied. All rats are individually housed in a temperature and humidity controlled room and maintained on a 12 hour light/dark cycle. Two to three weeks after surgery, rats undergo transthoracic echocardiography for determination of ejection fraction (EF %) and left ventricle dimensions (LVD) using a Vevo 2100 ultrasound system. Rats are randomized across treatment groups according to EF % and LVD.

Measurements of EF % and LVD are expressed as mean values±standard error (SE). Statistical analysis is performed with JMP® 13 software (SAS Institute, Inc.; Cary, NC) and Dunnett's Test is used for statistical comparisons across treatment groups. Statistical significance is accepted at P<0.05.

Study design for Determination of Example 9 Plasma Concentration for Nonclinical efficacy. At an infusion rate of 10 μl/h, Example 9 or vehicle (1× Dulbecco's phosphate-buffered saline [DPBS]) is administered subcutaneously (SC) continuously for 4 days through Alzet® pumps (Model 2ML1; Alzet® Osmotic Pumps; Cupertino, CA). The dose levels administered for Example 9 are 0.22, 0.73, 2.18, and 7.28 mg/kg/day using pump infusion. On Day 4, blood samples are collected to determine plasma concentration and the infusion pump is removed. Seven days after dosing started, cardiac function (EF %) and structure (LVD) are evaluated for all animals. Fourteen days after dosing started, EF % and LVD are evaluated for vehicle-treated and two highest dose groups.

Results. Example 9 treatment demonstrates a dose-dependent improvement in cardiac function (EF %) when administered for 96 hours using the osmotic pump (Table 10). High-dose groups administered 2.18 and 7.28 mg/kg/day, exhibit improved cardiac function for 2 weeks post-infusion started (Table 10). These doses achieve steady state plasma concentrations of 29.62 and 72.24 nM, respectively (Table 11). All treated MI animals exhibit less LVD dilatation compared to the vehicle group (Table 10).

TABLE 10

Effect of 96-Hour Infusion on EF in a Rat Model of HFrEF.

Ejection Fraction

| | Baseline | | 7 days after dosing started | | 14 days after dosing started | |
|---|---|---|---|---|---|---|
| Dose (mg/kg/day) | MEAN | s.e. | MEAN | s.e. | MEAN | s.e. |
| Sham, N = 3 | 70.2 | 6.42 | 68.1 | 4.64 | ND | ND |
| Vehicle, N = 7 | 41.7 | 1.97 | 39.6 | 1.92 | 39.6 | 1.73 |
| 0.22, N = 5 | 41.6 | 2.57 | 43.9 | 2.04 | ND | ND |
| 0.73, N = 7 | 42.3 | 1.42 | 45.8 | 2.09 | ND | ND |
| 2.18, N = 7 | 41.4 | 1.90 | 48.9* | 1.72 | 45.5 | 1.61 |
| 7.28, N = 7 | 41.1 | 1.06 | 49.8* | 2.10 | 48.0* | 2.08 |

Left Ventricle Diameter (end diastole)

| | Baseline | | 7 days after dosing started | | 14 days after dosing started | |
|---|---|---|---|---|---|---|
| Dose (mg/kg/day) | MEAN | s.e. | MEAN | s.e. | MEAN | s.e. |
| Sham, N = 3 | 7.21 | 0.51 | 7.49 | 0.76 | ND | ND |
| Vehicle, N = 7 | 7.56 | 0.35 | 7.94 | 0.26 | 7.90 | 0.25 |
| 0.22, N = 5 | 7.51 | 0.42 | 7.53 | 0.57 | ND | ND |
| 0.73, N = 7 | 7.55 | 0.27 | 7.83 | 0.30 | ND | ND |
| 2.18, N = 7 | 7.50 | 0.34 | 7.68 | 0.24 | 7.75 | 0.19 |
| 7.28, N = 7 | 7.60 | 0.29 | 7.52 | 0.31 | 7.67 | 0.19 |

Abbreviations:
N = number of animals;
ND = not determined;
SE = standard error.
*p < 0.05 vs vehicle.

TABLE 11

Exposure in Rat Plasma Following 96 Hours of Infusion.

| Dose (mg/kg/day) | Mean (nM) | Standard Deviation |
|---|---|---|
| 0.22 | 2.59 | 0.71 |
| 0.73 | 9.94 | 1.59 |
| 2.18 | 29.62 | 4.86 |
| 7.28 | 72.24 | 13.66 |

Study design for Determination of Infusion Duration for Nonclinical efficacy. At an infusion rate of 10 μl/h, 2.18 mg/kg/day of Example 9 or vehicle (DPBS) is administered SC for 48, 72, or 96 h through Alzet® pumps. At the end of designated infusion phase, blood samples are collected to determine plasma concentration and the infusion pump is removed. Seven days after dosing started, cardiac function (EF %) and structure (LVD) are evaluated for all animals.

Results. As seen in Table 12, in this study Example 9 treatment demonstrates an infusion duration-dependent improvement in cardiac function when administered for 48 to 96 h using the Alzet® pump. Example 9 infusion for 72 h and 96 h results in significant EF improvements on Day 7 after dosing started. All treated MI animals show less LVD dilatation compared to the vehicle group.

TABLE 12

Effect of Example 9 Infusion for Multiple Durations on Cardiac Function.

| | Ejection Fraction | | | |
|---|---|---|---|---|
| | Baseline | | 7 days after dosing started | |
| Duration Time (hours) | MEAN | s.e. | MEAN | s.e. |
| Vehicle, N = 8 | 40.8 | 2.80 | 39.2 | 2.78 |
| 48, N = 8 | 40.6 | 1.26 | 42.6 | 1.35 |
| 72, N = 9 | 41.0 | 1.96 | 44.6* | 1.69 |
| 96, N = 9 | 41.8 | 1.77 | 46.2* | 2.19 |

| | Left Ventricle Diameter (end diastole) | | | |
|---|---|---|---|---|
| | Baseline | | 7 days after dosing started | |
| Duration Time (hours) | MEAN | s.e. | MEAN | s.e. |
| Vehicle, N = 8 | 7.49 | 0.20 | 8.10 | 0.24 |
| 48, N = 8 | 7.52 | 0.29 | 7.68 | 0.30 |
| 72, N = 9 | 7.55 | 0.21 | 7.87 | 0.20 |
| 96, N = 9 | 7.44 | 0.16 | 7.70 | 0.22 |

Abbreviations:
N = number of animals;
ND = not determined;
SE = standard error. *$p < 0.05$ vs vehicle.

TABLE 13

Exposure in Rat Model of Myocardial Infarction Plasma Following Example 9 Infusion.

| Infusion Time (hours) | Mean (nM) | Standard Deviation |
|---|---|---|
| 48 | 40.13 | 6.37 |
| 72 | 47.28 | 17.85 |
| 96 | 31.42 | 9.86 |

Nonclinical data showed that LVEF improved in the rat model of HFrEF when plasma concentrations of Example 9 were maintained at 3 to 100 nM for a duration of 72 to 96 hours.

Effects of Example 10 on Cardiac Function and Structure in Rat MI Model

A nonclinical efficacy pharmacology study is conducted in a rat model of heart failure with reduced ejection fraction (HFrEF) to evaluate cardiac function and structure changes after captopril treatment, Example 10 treatment or combination treatment.

Methods. Male Sprague Dawley rats with surgically induced myocardial infarction are purchased and anesthetized and positively ventilated throughout the procedure. An incision is made between the fourth and fifth ribs, revealing the heart. The left coronary artery is permanently ligated. All rats are individually housed in a temperature and humidity controlled room and maintained on a 12 hour light/dark cycle. Two to three weeks after surgery, rats undergo transthoracic echocardiography for determination of ejection fraction (EF %) and left ventricle dimensions (LVD) using a Vevo 2100 ultrasound system. Rats are randomized across treatment groups according to EF % and LVD.

Measurements of EF % and LVD are expressed as mean values±standard error (SE). Statistical analysis is performed with JMP® 13 software (SAS Institute, Inc.; Cary, NC) and Dunnett's Test is used for statistical comparisons across treatment groups. Statistical significance is accepted at $P<0.05$.

Study design. Three weeks after MI surgery, animals are randomized to 2 treatment groups (Placebo or captopril, 2 g/L in drinking water, ad lib) according to EF % and LVD. Three weeks and four weeks after dosing starts, cardiac function (EF %) and structure (LVD) are evaluated by transthoracic echocardiography. Animals are further randomized to additional groups based on cardiac function (EF %) and structure (LVD) to the following groups: Placebo, Example 10, captopril and Example 10+captopril. Animals in the Example 10 groups receive a single injection on week 4 after the $2^{nd}$ randomization. Cardiac function (EF %) and structure (LVD) are evaluated on week 5 and 6.

Results. Results are provided in Table 14.

TABLE 14

Effects of captopril, a single injection of Example 10 or combination therapy on EF in a Rat Model of Heart Failure with reduced Ejection Fraction.

| | Ejection Fraction | | | | | | | | | |
|---|---|---|---|---|---|---|---|---|---|---|
| | Baseline | | Week 3 | | | Week 4 | | Week 5 | | Week 6 | |
| | AVG | s.e. | AVG | s.e. | | AVG | s.e. | AVG | s.e. | AVG | s.e. |
| Vehicle | 38.2 | 1.42 | 32.8 | 1.55 | Vehicle | 33.4 | 2.49 | 30.0 | 2.70 | 29.9 | 2.43 |
| Captopril | 39.1 | 1.30 | 38.4 | 2.43 | Captopril | 36.1 | 2.66 | 36.2 | 3.23 | 34.6 | 3.09 |
| | | | | | Example 10 | 33.3 | 2.06 | 46.5* | 3.68 | 46.0* | 2.46 |
| | | | | | Example 10 + Captopril | 35.8 | 1.96 | 47.3* | 1.97 | 46.7* | 2.45 |

TABLE 14-continued

Effects of captopril, a single injection of Example 10 or combination therapy on EF in a Rat Model of Heart Failure with reduced Ejection Fraction.

| | Left Ventricle Diameter (end diastole) | | | | | | | | | | |
|---|---|---|---|---|---|---|---|---|---|---|---|
| | Baseline | | Week 3 | | | Week 4 | | Week 5 | | Week 6 | |
| | AVG | s.e. | AVG | s.e. | | AVG | s.e. | AVG | s.e. | AVG | s.e. |
| Vehicle | 8.75 | 0.25 | 9.00 | 0.18 | Vehicle | 9.25 | 0.44 | 10.16 | 0.46 | 9.92 | 0.40 |
| Captopril | 8.66 | 0.16 | 8.57 | 0.14 | Captopril | 8.64 | 0.29 | 8.64* | 0.24 | 8.71* | 0.21 |
| | | | | | Example 10 | 9.33 | 0.24 | 9.35 | 0.37 | 9.01 | 0.25 |
| | | | | | Example 10 + Captopril | 8.82 | 0.12 | 8.51* | 0.23 | 8.41* | 0.28 |

Abbreviations:
AVG = mean.
s.e. = standard error.
*p < 0.05 vs vehicle.

As seen in Table 14, while captopril treatment slowed down cardiac function decline over the course of 6 weeks of treatment (not statistically significant), Example 10 treatment significantly improved cardiac function (EF %) and reduced LV dilation after a single treatment.

Effects of Example 11 on Cardiac Function and Structure in Rat MI Model

A nonclinical efficacy pharmacology study is conducted in a rat model of heart failure with reduced ejection fraction (HFrEF) to identify dose-response relationship for Example 11.

Method. Male Sprague Dawley rats with surgically induced myocardial infarction are purchased from Charles River. Briefly, the rats are anesthetized and positively ventilated throughout the procedure. An incision is made between the fourth and fifth ribs, revealing the heart. The left coronary artery is permanently ligated. The sham-operated animals undergo the same procedure except the silk suture is placed around the left coronary artery without being tied. All rats are individually housed in a temperature and humidity controlled room and maintained on a 12 hour light/dark cycle. Three weeks after surgery, rats undergo transthoracic echocardiography for determination of ejection fraction (EF %) and left ventricle dimensions (LVD) using a Vevo 2100 ultrasound system. Rats are randomized across treatment groups according to EF % and LVD.

Measurements of EF % and LVD are expressed as mean values±standard error (SE). Statistical analysis is performed with JMP® 13 software (SAS Institute, Inc.; Cary, NC) and Dunnett's Test is used for statistical comparisons across treatment groups. Statistical significance is accepted at P<0.05.

Study design. Two to three weeks after MI surgery, animals are allocated to treatment groups and treated with a single injection of vehicle (DPBS) or one of the 3 dose levels (0.3, 1, 3 mg/kg) of Example 11. Seven days, 14 days and 21 days after dosing, cardiac function (EF %) and structure (LVD) are evaluated for all animals.

Results. Results are provided in Table 15.

TABLE 15

Effect of Example 11 on EF in a Rat Model of Heart Failure with reduced Ejection Fraction.

| | Ejection Fraction | | | | | | | |
|---|---|---|---|---|---|---|---|---|
| | Baseline | | 7 days after dosing | | 14 days after dosing | | 21 days after dosing | |
| Dose | MEAN | s.e. | MEAN | s.e. | MEAN | s.e. | MEAN | s.e. |
| Sham, N = 5 | 73.7 | 2.24 | 72.5 | 1.76 | 71.8 | 0.81 | 71.9 | 3.60 |
| Vehicle, N = 8 | 45.0 | 1.50 | 41.2 | 2.90 | 38.4 | 1.98 | 37.8 | 1.98 |
| 0.3 mg/kg, N = 8 | 45.4 | 2.46 | 50.1* | 3.22 | 42.6 | 1.43 | 36.4 | 1.43 |
| 1 mg/kg, N = 8 | 46.6 | 1.86 | 52.4* | 2.61 | 42.2 | 2.77 | 39.7 | 2.77 |
| 3 mg/kg, N = 8 | 45.8 | 1.48 | 54.7* | 2.11 | 54.0* | 2.49 | 39.6 | 2.49 |

Abbreviations:
N = number of animals;
s.e. = standard error.
*p < 0.05 vs vehicle.

As seen in Table 15, Example 11 treatment demonstrates a dose-dependent improvement in cardiac function (EF %). The high-dose group exhibits improved cardiac function for 2 weeks post-treatment. No differences in LVD dilation are observed across groups during the course of the study (data not shown).

Effects of Examples 9-11 on Cardiac Toxicity

Toxicology studies are conducted on Examples 9-11 in rats and/or cynomolgus monkeys. Example 10 is administered to rats in a single SC injection of 0.3 mg/kg, which results in detectable plasma concentrations for longer than 168 hours. Rats are sacrificed, and inspections of tissue reveal cardiac degeneration and necrosis. Example 11 is administered to rats in a single SC injection of 30 mg/kg; plasma concentration was undetectable at 96 hours. Rats are sacrificed, and inspections of tissue reveal no evidence of cardiac degeneration and/or necroses. Example 11 is administered in a single 3 mg/kg dose to male and female monkeys by SC bolus injection. In contrast to its pharmacokinetics in rats, the single injections in monkeys results in detectable plasma concentrations that take longer than 168 hours to be cleared. Monkeys are sacrificed, and inspections of tissue reveal cardiac degeneration and necrosis. Example 9, which shows a half-life after SC administration of less than an hour in rats, is administered in doses resulting in plasma concentrations ranging from 3-300 nM for 96-168 hours by subcutaneously (SC) implanted pumps. Rats are sacrificed, and inspections of tissue reveal no evidence of cardiac degeneration and/or necroses. Example 9, which has a half life after SC administration of less than 5 hours in monkeys, is administered in doses resulting in plasma concentrations ranging from 30-1000 nM for 96 hours to male and female monkeys by surgically placed SC or intravenous (IV) catheter. Monkeys are sacrificed, and inspections of tissue reveal no evidence of cardiac toxicity and/or necroses. These data indicate that NRG4 compounds may be administered without causing cardiac toxicity by limiting the duration of exposure to the NRG4 compound.

```
Sequences

SEQ ID NO: 1 - Human NRG4
DHEEPCGPSH KSFCLNGGLC YVIPTIPSPF CRCVENYTGA RCEEVFL

SEQ ID NO: 2 - NRG4 Compound
X0GHEEPCGX8SHKSFCLNGGLCYX22IPTX26PSPFCRCVX35NYTGARCEX44VFL
wherein:
X0 is selected from the group consisting of T, PT, MPT, S, GS, GGS, GGGS, and
(GGGGXλ)n wherein Xλ, is Q, A, E or S and n = 1-5 (SEQ ID NO: 5), or is absent;
X8 is E or P;
X22 is Q or V;
X26 is F or I;
X35 is E or A; and
X44 is H, K or E.

SEQ ID NO: 3 Human NRG4 Full Sequence As Expressed
MPTDHEEPCG PSHKSFCLNG GLCYVIPTIP SPFCRCVENY TGARCEEVFL
PGSSIQTKSN LFEAFVALAV LVTLIIGAFY FLCRKGHFQR ASSVQYDINL
VETSSTSAHH SHEQH SEQ ID NO: 4 - NRG4 Compound
GHEEPCGPSH KSFCLNGGLC YQIPTIPSPF CRCVENYTGA RCEKVFL SEQ ID NO: 5 - Glycine rich peptide or linker
(GGGGXλ)n
wherein:
Xλ, is Q, A, E or S; and
n is 1-5.

SEQ ID NO: 6 - IgG Fc region
ECPPCPAPPVAGPSVFLFPPKPKDTLMISRTPEVTCVVVDVSHEDPEVQFNWYVD
GVEVHNAKTKPREEQFNSTFRVVSVLTVVHQDWLNGKEYKCKVSNKGLPAPIEK
TISKTKGQPREPQVYTLPPSREEMTKNQVSLWCLVKGFYPSDIAVEWESNGQPEN
NYKTTPPVLDSDGSFFLYSKLTVDKSRWQQGNVFSCSVMHEALHNHYTQKSLSL
SPG SEQ ID NO: 7 - IgG Fc region
ECPPCPAPPVAGPSVFLFPPKPKDTLMISRTPEVTCVVVDVSHEDPEVQFNWYVD
GVEVHNAKTKPREEQFNSTFRVVSVLTVVHQDWLNGKEYKCKVSNKGLPAPIEK
TISKTKGQPREPQVYTLPPSREEMTKNQVSLSCAVKGFYPSDIAVEWESNGQPEN
NYKTTPPVLDSDGSFFLVSKLTVDKSRWQQGNVFSCSVMHEALHNHYTQKSLSL
SPG SEQ ID NO: 8 - IgG Fc region
ECPPCPAPPVAGPSVFLFPPKPKDTLMASRTPEVTCVVVDVSHEDPEVQFNWYVD
GVEVHNAKTKPREEQFNSTFRVVSVLTVVHQDWLNGKEYKCKVSNKGLPAPIEK
TISKTKGQPREPQVYTLPPSREEMTKNQVSLWCLVKGFYPSDIAVEWESNGQPEN
NYKTTPPVLDSDGSFFLYSKLTVDKSRWQQGNVFSCSVMHEALHNAYTQKSLSL
SPG SEQ ID NO: 9 - IgG Fc region
ECPPCPAPPVAGPSVFLFPPKPKDTLMASRTPEVTCVVVDVSHEDPEVQFNWYVD
GVEVHNAKTKPREEQFNSTFRVVSVLTVVHQDWLNGKEYKCKVSNKGLPAPIEK
TISKTKGQPREPQVYTLPPSREEMTKNQVSLSCAVKGFYPSDIAVEWESNGQPEN
NYKTTPPVLDSDGSFFLVSKLTVDKSRWQQGNVFSCSVMHEALHNAYTQKSLSL
SPG SEQ ID NO: 10 - NRG4 Compound
GGGGSGGGGSGGGGS GHEEPCGPSH KSFCLNGGLC YVIPTIPSPF
CRCVENYTGA RCEEVFL SEQ ID NO: 11 - NRG4 Compound
GGGGSGGGGSGGGGS GHEEPCGESH KSFCLNGGLC YVIPTIPSPF
CRCVENYTGA RCEEVFL
```

| Sequences |
|---|
| SEQ ID NO: 12 - NRG4 Compound<br>GGGGSGGGGSGGGGS GHEEPCGPSH KSFCLNGGLC YQIPTIPSPF<br>CRCVENYTGA RCEEVFL |
| SEQ ID NO: 13 - NRG4 Compound<br>GGGGSGGGGSGGGGS GHEEPCGPSH KSFCLNGGLC YVIPTFPSPF<br>CRCVENYTGA RCEEVFL |
| SEQ ID NO: 14 - NRG4 Compound<br>GGGGSGGGGSGGGGSGHEEPCGPSH KSFCLNGGLCYVIPTIPSPFCRCVANYTGA<br>RCEEVFL |
| SEQ ID NO: 15 - NRG4 Compound<br>GGGGSGGGGSGGGGSGHEEPCGPSHKSFCLNGGLCYVIPTFPSPFCRCVENYTGA<br>RCEKVFL |
| SEQ ID NO: 16 - NRG4 Compound<br>GGGGSGGGGSGGGGSGHEEPCGPSHKSFCLNGGLCYVIPTFPSPFCRCVENYTGA<br>RCEHVFL |
| SEQ ID NO: 17 - NRG4 Compound<br>GGGGSGGGGSGGGGSGHEEPCGESHKSFCLNGGLCYVIPTFPSPFCRCVENYTGA<br>RCEEVFL |
| SEQ ID NO: 18 - NRG4 Compound<br>GGGGSGHEEPCGPSHKSFCLNGGLCYQIPTIPSPFCRCVENYTGARCEKVFL |
| SEQ ID NO: 19 - NRG4 Compound<br>GGGGSGGGGSGGGGSGHEEPCGPSHKSFCLNGGLCYQIPTIPSPFCRCVENYTGA<br>RCEKVFL |
| SEQ ID NO: 20<br>GGGS |

We claim:

1. A compound comprising the formula:

GHEEPCGX$_8$SHKSFCLNGGLCYX$_{22}$IPTX$_{26}$PSPFCRCVX$_{35}$NYTGARC EX$_{44}$VFL wherein:
$X_8$ is E or P;
$X_{22}$ is Q or V;
$X_{26}$ is F or I;
$X_{35}$ is E or A; and
$X_{44}$ is H, K or E (SEQ ID NO:2) and wherein the compound optionally comprises an N-terminal extension selected from the group consisting of T, PT, MPT, S, GS, GGS, GGGS (SEQ ID NO:20), and (GGGGX$_\lambda$)$_n$ wherein X$_\lambda$ is Q, A, E or S and n=1-5 (SEQ ID NO:5).

2. The compound of claim 1 wherein $X_8$ is P; $X_{22}$ is V; $X_{26}$ is I; $X_{35}$ is E; and $X_{44}$ is E.

3. The compound of claim 1 wherein $X_8$ is E; $X_{22}$ is V; $X_{26}$ is I; $X_{35}$ is E; and $X_{44}$ is E.

4. The compound of claim 1 wherein $X_8$ is P; $X_{22}$ is Q; $X_{26}$ is I; $X_{35}$ is E; and $X_{44}$ is E.

5. The compound of claim 1 wherein $X_8$ is P; $X_{22}$ is V; $X_{26}$ is F; $X_{35}$ is E; and $X_{44}$ is E.

6. The compound of claim 1 wherein $X_8$ is P; $X_{22}$ is V; $X_{26}$ is I; $X_{35}$ is A; and $X_{44}$ is H or E.

7. The compound of claim 1 wherein $X_8$ is P; $X_{22}$ is V; $X_{26}$ is F; $X_{35}$ is E; and $X_{44}$ is K.

8. The compound of claim 1 wherein $X_8$ is P; $X_{22}$ is V; $X_{26}$ is F; $X_{35}$ is E; and $X_{44}$ is H.

9. The compound of claim 1 wherein $X_8$ is E; $X_{22}$ is V; $X_{26}$ is F; $X_{35}$ is E; and $X_{44}$ is E.

10. The compound of claim 1, wherein $X_8$ is P; $X_{22}$ is Q; $X_{26}$ is I; $X_{35}$ is E; and $X_{44}$ is K.

11. The compound of claim 1 further comprising an IgG Fc region.

12. The compound of claim 11, wherein the compound comprises an N-terminal extension that is SEQ ID NO:5 wherein $X_\lambda$ is S and n=3, and wherein the IgG Fc region comprises a dimer of SEQ ID NO:6 and SEQ ID NO:7, wherein the N terminal amino acid of the N-terminal extension $X_0$ is fused to the C-terminal amino acid of SEQ ID NO:7.

13. The compound of claim 11, wherein the compound comprises an N-terminal extension that is SEQ ID NO:5 wherein $X_\lambda$ is S and n=3, and wherein the IgG Fc region comprises a dimer of SEQ ID NO:8 and SEQ ID NO:9, wherein the N terminal amino acid of the N-terminal extension is fused to the C-terminal amino acid of SEQ ID NO:9.

14. The compound of claim 1 wherein the compound comprises an amino acid sequence selected from the group consisting of: SEQ ID NO:4, SEQ ID NO:10, SEQ ID NO:11, SEQ ID NO:12, SEQ ID NO:13, SEQ ID NO:14, SEQ ID NO:15, SEQ ID NO: 16, SEQ ID NO:17, and SEQ ID NO:19.

15. The compound of claim 1, wherein the compound has HER4 binding-related activity which is greater than that of native human NRG4 and at least 70% that of the maximal activity of native human NRG1.

16. The compound of claim 15, wherein the compound has no HER3 binding-related activity.

17. A pharmaceutical composition comprising the compound of claim 1 and a pharmaceutically acceptable carrier, diluent, or excipient.

18. A pump device comprising the compound of claim 1.

19. A method of treating heart failure with reduced ejection fraction (HFrEF) in a patient in need thereof, comprising administering to the patient a neuregulin 4 (NRG4) compound of claim 1 in an amount sufficient to provide therapeutically effective serum concentrations of said NRG4 compound for 24-96 hours.

20. The method of claim 19 wherein the efficacy:administration ratio ranges from about 2 to about 50.

21. The method of claim 19, wherein the NRG4 compound is administered once quarterly (Q3M) by continuous subcutaneous infusion for 24-96 hours.

22. The method of claim 19, wherein the NRG4 compound is administered by patch pump.

23. The method of claim 19, wherein treatment is continued for at least 1 year.

24. The method of claim 19, wherein the method results in a significant increase in left ventricular ejection fraction (LVEF).

25. The method of claim 19, wherein the method results in a significant reduction in global longitudinal strain (GLS).

26. The method of claim 19, wherein the method results in a significant improvement in left ventricular end-diastolic volume (LVEDV).

27. The method of any claim 19, wherein the method results in a significant reduction in risk of cardiovascular (CV) death.

28. The method of claim 19, wherein the method results in a significant reduction in risk of heart failure (HF)-related in hospitalization.

29. The method of claim 19, wherein the patient has New York Heart Association (NYHA) II or III heart failure.

\* \* \* \* \*

UNITED STATES PATENT AND TRADEMARK OFFICE
CERTIFICATE OF CORRECTION

| | | |
|---|---|---|
| PATENT NO. | : 12,145,972 B2 | Page 1 of 1 |
| APPLICATION NO. | : 17/559430 | |
| DATED | : November 19, 2024 | |
| INVENTOR(S) | : Jonathan Wesley Day et al. | |

It is certified that error appears in the above-identified patent and that said Letters Patent is hereby corrected as shown below:

In the Claims

Column 46, Line 28, in Claim 27, delete "of any" and insert --of--.

Signed and Sealed this
Eighteenth Day of March, 2025

Coke Morgan Stewart
*Acting Director of the United States Patent and Trademark Office*